(12) United States Patent
Petropoulos et al.

(10) Patent No.: US 6,489,098 B1
(45) Date of Patent: Dec. 3, 2002

(54) MEANS AND METHODS FOR MONITORING NUCLEOSIDE REVERSE TRANSCRIPTASE INHIBITOR ANTIRETROVIRAL THERAPY AND GUIDING THERAPEUTIC DECISIONS IN THE TREATMENT OF HIV/AIDS

(75) Inventors: Christos J. Petropoulos, Half Moon Bay, CA (US); Jeannette Whitcomb, San Mateo, CA (US)

(73) Assignee: ViroLogic, Inc., South San Francisco, CA (US)

( * ) Notice: Subject to any disclaimer, the term of this patent is extended or adjusted under 35 U.S.C. 154(b) by 0 days.

(21) Appl. No.: 09/339,357

(22) Filed: Jun. 23, 1999

Related U.S. Application Data
(60) Provisional application No. 60/090,547, filed on Jun. 24, 1998.

(51) Int. Cl.$^7$ ................................. C12Q 1/70
(52) U.S. Cl. .................... 435/6; 435/91.33; 514/45; 514/49; 514/50; 536/24.3
(58) Field of Search .................. 435/6, 87, 91.33, 435/113, 116, 183; 514/45, 49, 50; 530/300, 350; 536/24.3; 935/19, 20

(56) References Cited

U.S. PATENT DOCUMENTS
5,837,464 A    11/1998   Capon et al. ................... 435/6

OTHER PUBLICATIONS

Ping–Fang et al. Genotypic and phenotypic analysis of human immunodeficiency virus type 1 isolates from patentients on prolonged stavudine therapy. Journal of Infectious Diseases (1994) vol. 170, pp. 1157–1164.*

Kuritzkes D.R. Clinical signigficance of drug resistance in HIV–1 infection. AIDS (1996) vol. 10, S27–S31.*

Iversen et al. Multidrug–resistant immunodeficiency virus type 1 strains resulting from combination antiretroviral therapy. Journal of Virology. vol. 70, No. 2 (1996) pp. 1086–1090.*

Frenkel et al. Specific, sensitive, and rapid assay for human immunodeficiency virus type 1 pol mutations associated with resistance to zidovudine and didanosine. Journal of Clinical Immunology. vol. 33, No. 2 (1995) pp. 342–347.*

Fitzgibbon et al. Human Immunodeficiency virus type 1 pol gene mutations in an AIDS pateint treated with multiple antiretroviral drugs. Journal of Virology, vol. 67, No. 12 (1993) pp. 7271–7275.*

Ahluwalia, G. S., et al. (1996) "2', 3'–Didehydro–3'–deoxythymidine: Regulation of its Metabolic Activation by Modulators of Thymidine–5'–triphosphate Biosynthesis" *Mol. Pharm.* 50: 160–165 (Exhibit 1).

Kleim, J., et al. (1997) "In vitro Selection for Different Mutational Patterns in the HIV–1 Reverse Transcriptase Using High and Low Selective Pressure of the Nonnucleoside Reverse Transcriptase inhibitor HBY 097" *Virology.* 231: 112–118 (Exhibit 2).

Krebs, R., et al. (1997 "Single–Step Kinetics of HIV–1 Reverse Transcriptase Mutants Responsible for Virus Resistance to Nucleoside Inhibitors Responsible for Virus Resistance to Nucleoside Inhibitors Zidovudine and 3–TC" *Biochemistry* 36: 10292–10300 (Exhibit 3).

International Search Report for PCT Application No. PCT/US99/14486, filed Jun. 23, 1999 (Exhibit B).

Appelt KR, et al, (1991) "Design of Enzyme Inhibitors Using Iterative Protein Crystallographic Analysis", *J. Med. Chem* 34:1925–1928 (Exhibit 2).

Back, KT, et al, (1996) "Reduce Replication of 3TC–Resistant HIV–1 Variants in Primary Cells Due to a Processivity Defect of the Reverse Transcriptase Enzyme", *EMBO* 15: 4040–4049 (Exhibit 3).

Barnes WM, (1994) "PCR Amplication of up to 35–kb DNA with High Fidelity and High Yeild from λ Bacteriophage Templates" *PNAS* 91:2216–2220 (Exhibit 4).

Bartenschlager R, et al, (1994) "Kinetic and Structural Analyses of Hepatitis C Virus Polyprotein Processing", *J. Virol* 68:5045–5055 (Exhibit 5).

Croteau G. et al (1997) "Impaired Fitness of Human Immunodeficiency Virus Type 1 Variants with High–Level Resistance to Protease Inhibitors" *J Virol* 71:1089–1096 (Exhibit 6).

DeClerg E, (1992) "HIV Inhibitors Targeted at the Revest Transcriptase", *AIDS Res. Hum Retrovin.*8:119–134(Exhibit 7).

Doyon L, et al, (1996) "Second Locus Involved in Human Immunodeficiency Virus Type 1 Resistance to Protease Inhibitors", *J Virol* 70:3763–3769 (Exhibit 8).

Gerondelis P, et al, (1999) "The P236L Delavirdine–Resistant Human Immunodeficiency Virus Type 1 Mutant is Replication Defective and Demonstrates Alternations in both RNA 5'–End–and DNA 3';–End–Directed RNase H Activities", *J Virol* 73: 5803–5813 (Exhibit 9).

(List continued on next page.)

*Primary Examiner*—Jeffrey Stucker
*Assistant Examiner*—Ulrike Winkler
(74) *Attorney, Agent, or Firm*—John P. White; Cooper & Dunham LLP

(57) ABSTRACT

This invention relates to antiviral drug susceptibility and resistance tests to be used in identifying effective drug regimens for the treatment of human immunodeficiency virus (HIV) infection and acquired immunodeficiency syndrome (AIDS) and further relates to the means and methods of monitoring the clinical progression of HIV infection and its response to antiretroviral therapy, particularly nucleoside reverse transcriptase inhibitor therapy using phenotypic susceptibility assays or genotypic assays.

13 Claims, 13 Drawing Sheets

OTHER PUBLICATIONS

Harrigan PR, et al, (1998) "Relative Republication Fitness of Zidovudine–Resistant Human Immunodeficiency Virus Type 1 Isolates In Vitro", *J Virol* 72:3773–3778 (Exhibit 10).

Ho DD, et al, (1994) "Characterization of Human Immunodeficiency Virus Type 1 Variants with Increased Resistance to a $C_2$–Symmetric Protease Inhibitor", *J Virol* 68:2016–2020 (Exhibit 11).

Kim EE, et al, (1995)"Crystal Structure of HIV–1 Protease in Complex with VX–478, a Potent and Orally Bioavailable Inhibitor of the Enzyme", *J Am Chem* Soc. 117: 1181–1182 (Exhibit 12).

Kosalaraksa P, et al, (1999) "Comparative Fitness of Multi–Dideoxynucleoside–Resistant Human Immunodeficiency Virus Type 1 (HIV–1) in an In Vitro Competitive HIV–1 Replication Assay", *J Virol* 73:5356–5363 (Exhibit 13).

Mammamo F, et al, (1998) "Resistance–Associated Loss of Viral Fitness in Human Immunodeficiency Virus Type 1: Phenotypis Analysis of Protease and gag Coevoluation inProtease Inhibitor–Treated Patients", *J Virol* 72:7632–7637 (Exhibit 14).

Maschera B, et al, (1996) "Mutations in the Viral Protease that Confer Resistance to Saquinavir Increase the Dissociation Rate Constant of the Protease–Saquinavir Complex", *J Bio Chem* 271:33231–33235 (Exhibit 15).

Mulligan RC and Berg P, (1980) "Expression of a Bacterial Gene in Mammalian Cells", *Science* 209:1422–11427 (Exhibit 16).

Sakar G and Sommer S, (1990) "The "Megaprimer" Method of Site–Directed Mutagenesis", 8(4):404–407 (Exhibit 17).

Southern PJ and Berg P (1982) "Transformation of Mammalian Cells to Antibotic Resistance with a Bacterial Gene Under Control of the SV40 Early Region Promoter", *Appl Genet* 1:327–341 (Exhibit 18).

Sugden B, et al, (1985)"A Vector taht Replicates as a Plasmid and can be Efficiently Selected in B–Lymphoblasts Transformed by Epstein–Barr Virus", *Mol Cell Bio* 5:410–413 (Exhibit 19).

Vacca JP, et al, (1994) "L–735,524: An Orally Bioavailable Human Immunodeficiency Virus Type 1 Protease Inhibitor", *PCAS* 91:4096–4100 (Exhibit 20).

Zennou V, (1998) "Loss of Viral Fitness Associated with Multiple Gag and Gag–Pol Processing Defects in Human Immunodeficiency Virus Type 1 Variants Selected for Resistance to Protease Inhibitors In Vivo", *J. Viro.,* 72:3300–3306 (Exhibit 21).

Zhang Y, et al, (1997) "Drug Resistance During Indinavir Therapy is Caused by Mutations in the Protease Gene and in its Gag Substrate Cleavage Sites", *J Virol* 71:6662–6670 (Exhibit 22).

Boucher CAB, et al, (1993)"High–Level Resistance to (−) Enantiomeric 2'–Deoxy–3'–Thiacytidine In Vitro is Due to One Amino Acid Substitution in the Catalytic Site of Human Immunodeficiency Virus Type 1 Reverse Transcriptase", *Antimicrob Agents Chemother,* 37:2231–2234(Exhibit 23).

Boucher CAB, et al, (1990)"Zidovudine sensitivity of human immunodeficiency viruses from high–risk, symptom–free individuals during therapy", *Lancet* 336:585–590 (Exhibit 24).

Coffin JM, (1995) "HIV Population Dynamics in Vivo: Implications for Genetic Variation, Pathogenesis, and Therapy", *Science* 267:483–489 (Exhibit 25).

Craig C and Moyle G, (1997)"The development of resistance of HIV–1 to zalcitabine", *AIDS* 11:271–279 (Exhibit 26).

DeJong MD, et al, (1996) "Host–parasite Dynamics and Outgrowth of Virus Containing a Single K7OR Amino Acid Change in Reverse Transcriptase are Responsible for the Loss of Human Immunodeficiency Virus Type 1 RNA Load Suppression by Zidovudine", *PNAS* 93:9501–9506 (Exhibit 27).

Frost SDW and Mclean AR, (1994) "Quasispecies dynamics and the emergence of drug resistance during zidovudine therapy of HIV infection", *AIDS* 8:323–332 (Exhibit 28).

Goulden MG, et al, (1996) "Selection In Vitro of an HIV–1 Variant Resistant to Both Lamivudine (3TC) and Zidvudine", *AIDS* 10:101–102 (Exhibit 29).

Gu Z, et al, (1994) "Identification of Novel Mutations that Confer Drug Resistance In the Human Immunodeficiency Virus Polymerase Gene", *Leukemia* 8(1):166–169 (Exhibit 30).

Kellam P, et al, (1994) "Zidovudine Treatment Results in the Selection of Human Immunodeficiency Virus Type 1 Variants whose Genotypes Confer Increasing Levels of Drug Resistance", *J Gen Virol* 75:341–351 (Exhibit 31).

Larder BA, (1992) "3'–Azido–3'–Deoxythymidine Resistance Suppressed by a Mutation Conferring Human Immunodeficiency Virus Type 1 Resistance to Nonnucleoside Reverse Transcriptase Inhibitors", *Antimicrob Agents Chemother* 36: 2664–2669 (Exhibit 32).

Larder BA, et al, (1991) "Zidovudine resistance predicted by direct detection of mutations in DNA from HIV–infected lymphocytes", *AIDS* 5:137–144 (Exhibit 33).

Larder BA, et al, (1995) "Potential Mechanism for Sustained Antiretroviral Efficacy of AZT–3TC Combination Therapy", *Science* 269:696–699 (Exhibit 34).

Lin PF, et al, (1994) "Genotypic and Phenotypic Analysis of Human Immunodeficiency Virus Type 1 Isolates from Patients on Prolonged Stavudine Therapy", *J Infect Disease* 170:1157–1164 (Exhibit 35).

Lopez–Galindez C, et al, (1991) "Characterization of genetic variation and 3'–azido–3'–deoxythymidine–resistance mutations of human immunodeficiency virus by the Rnase A mismatch cleavage method", *PNAS* 88:4280–4284 (Exhibit 36).

Mayers DL, et al, (1992) "Characterization of HIV Isolates Arising After Prolonged Zidovudine Therapy", *J Acq Imm Def Synd* 5:749–759 (Exhibit 37).

Mohri H, et al, (1993) "Quantitation of Zidovudine–Resistant Human Immunodeficiency Virus Type 1 in the Blood of Treated and Untreated Patients", *PNAS* 90:25–29 (Exhibit 38).

Moyle GJ (1996) "Use of Viral Resistance Patterns to Antiretroviral Drugs in Optimising Selection of Drug Combinations and Sequences", *Drugs* 52:168–185 (Exhibit 39).

Nájera I, et al, (1994) "Natural Occurrence of Drug Resistance Mutations in the Reverse Transcriptase of Human Immunodeficiency Virus Type 1 Isolates", *AIDS Res. Hum. Retroviruses* 10:1479–1488 (Exhibit 40).

Nájera I, et al, (1995) "pol Gene Quasispecies of Human Immunodeficiency Virus Mutations Associated with Drug Resistance in Virus from Patients Undergoing No Drug Therapy", *J Virol* 89:23–31 (Exhibit 41).

Shafer RW, et al, (1994) "Combination Therapy with Zidovudine and Didanosine Selects for Drug–Resistant Human Immunodeficiency Virus Type 1 Strains with Unique Patterns of pol Gene Mutations", *J Infect Disease* 169:722–729 (Exhibit 42).

Shirasaka T, et al, (1995) "Emergence of Human Immunodeficiency Virus Type 1 Variants with Resistance to Multiple Deoxynucleosides in Patients Receiving Therapy with Dideoxynucleosides", *PNAS* 92:2398–2402 (Exhibit 43).

Tisdale M, et al, (1993) "Rapid In Vitro Selection of Human Immunodeficiency Virus Type 1 Resistant to 3'–Thiacytidine Inhibitors due to a Mutation in the YMDD Region of Reverse Transcriptase", *PNAS* 90:5653–5656 (Exhibit 44).

Zhang D, et al, (1994) "Resistance to 2',3'–Dideoxycytidine Conferred by a Mutation in Codon 65 of the Human Immunodeficiency Virus Type 1 Reverse Transcriptase", *Antimicrob Agents Chemother* 38:282–287 (Exhibit 45).

* cited by examiner

Resistance Test Vector

HIV-1

Resistance Test Vector

Two Cell Assay

*Drug Resistance : NRTI, NNRTI, PI*

Site Directed Mutations: Multiple Mutations at RT Amino Acids 62, 69, 75

MEANS AND METHODS FOR MONITORING NUCLEOSIDE REVERSE TRANSCRIPTASE INHIBITOR ANTIRETROVIRAL THERAPY AND GUIDING THERAPEUTIC DECISIONS IN THE TREATMENT OF HIV/AIDS

This application claims priority of U.S. provisional application No. 60/090,547, filed Jun. 24, 1998, the content of which is hereby incorporated into this application by reference.

Throughout this application, various references are referred to within parentheses. Disclosures of these publications in their entireties are hereby incorporated by reference into this application to more fully describe the state of the art to which this invention pertains.

TECHNICAL FIELD

This invention relates to antiretroviral drug susceptibility and resistance tests to be used in identifying effective drug regimens for the treatment of human immunodeficiency virus (HIV) infection and acquired immunodeficiency syndrome (AIDS). The invention further relates to the means and methods of monitoring the clinical progression of HIV infection and its response to antiretroviral therapy using phenotypic or genotypic susceptibility assays. The Invention also relates to novel vectors, host cells and compositions for carrying out phenotypic susceptibility tests. The invention further relates to the use of various genotypic methodologies to identify patients whose Infection has become resistant to a particular antiretroviral drug regimen. This invention also relates to the screening of candidate antiretroviral drugs for their capacity to inhabit viruses, selected viral sequences and/or viral proteins. More particularly, this invention relates to the determination of nucleoside reverse transcriptase inhibitor resistance using phenotypic susceptibility tests and/or genotypic tests.

BACKGROUND OF THE INVENTION

HIV infection is characterized by high rates of viral turnover throughout the disease process, eventually leading to CD4 depletion and disease progression. Wei X, Ghosh S K, Taylor M E, et al. (1995) *Nature* 343, 117–122 and Ho D D, Naumann A U, Perelson A S, et al. (1995) *Nature* 373, 123–126. The aim of antiretroviral therapy is to achieve substantial and prolonged suppression of viral replication. Achieving sustained viral control is likely to involve the use of sequential therapies, generally each therapy comprising combinations of three or more antiretroviral drugs. Choice of initial and subsequent therapy should, therefore, be made on a rational basis, with knowledge of resistance and cross-resistance patterns being vital to guiding those decisions. The primary rationale of combination therapy relates to synergistic or additive activity to achieve greater inhibition of viral replication. The tolerability of drug regimens will remain critical, however, as therapy will need to be maintained over many years.

In an untreated patient, some $10^9$ new viral particles are produced per day. Coupled with the failure of HIV reverse transcriptase (RT) to correct transcription errors by exonucleolytic proofreading, this high level of viral turnover results in $10^{-4}$ to $10^{-3}$ mutations per day at each position in the HIV genome. The result is the rapid establishment of extensive genotypic variation. While some template positions or base pair substitutions may be more error prone (Mansky L M, Temin H M (1995) *J Virol* 69, 5087–5094) (Schinazi R F, Lloyd R M, Ramanathan C S, et al. (1994) *Antimicrob Agents Chemoter* 38, 268–274), mathematical modeling suggests that, at every possible single point, mutation may occur up to 10,000 times per day in infected individuals.

For antiretroviral drug resistance to occur, the target enzyme must be modified while preserving its function in the presence of the inhibitor. Point mutations leading to an amino acid substitution may result in change in shape, size or charge of the active site, substrate binding site or surrounding regions of the enzyme. Mutants resistant to antiretroviral agents have been detected at low levels before the initiation of therapy. (Mohri H, Singh M K, Ching W T W, et al. (1993) *Proc Natl Acad Sci USA* 90, 25–29) (Nájera I, Richman D D, Olivares I, et al. (1994) *AIDS Res Hum Retroviruses* 10, 479–1488) (Nájera I, Holguin A, Quinones-Mateu E, et al. (1995) *J Virol* 69, 23–31). However, these mutant strains represent only a small proportion of the total viral load and may have a replication or competitive disadvantage compared with wild-type virus. (Coffin J M (1995) *Science* 267, 483–489). The selective pressure of antiretroviral therapy provides these drug-resistant mutants with a competitive advantage and thus they come to represent the dominant quasispecies (Frost S D W, McLean A R (1994) *AIDS* 8, 323–332) (Kellam P, Boucher C A B, Tijnagal J M G H (1994) *J Gen Virol* 75, 341–351) ultimately leading to drug resistance and virologic failure in the patient.

Nucleoside Reverse Transcriptase Inhibitors

Seven nucleoside analogue HIV reverse transcriptase Inhibitors (zidovudine (ZVD: Retrovir, Glaxo Wellcome, Uxbridge, UK), zalcitabine (ddC: HIVID, Hoffman-LaRoche, Basle, Switzerland), didanosine (ddI: Videx, Bristol-Myers Squibb, Syracuse, N.Y., USA), stavudine (d4T: Zerit, Bristol-Myers Squibb, Syracuse, N.Y., USA), and lamivudine (3TC, Epivir), abacavir (ABC, Ziagen, Glaxo Wellcome), and adefovir (ADV, Preveon, Gilead Sciences) are currently licensed in Europe and the USA. Additionally, three NNRTIs, nevirapine (Viramune, Boehringer Ingelheim, Ingelheim am Rhein, Germany) and delavirdine (Rescriptor, Pharmacia & Upjohn, Kalamazoo, Mich., USA) and efavirenz (EPV,) are licensed in the USA. All these agents have demonstrated at least short-term antiviral activity and, therefore, it is not surprising that, as they exert a selective pressure on HIV, drug-resistant mutants arise during therapy. Whilst these drugs are normally used in combination regimens, many of the available resistance data arise from phase I/II monotherapy studies. Mutations observed during monotherapy may not accurately reflect mutations responsible for resistance that develops in the presence of pressure from several agents acting at the same site and, hence, on the same gene.

Novel Mutations

Whilst patterns of genotypic mutations associated with changes in phenotypic resistance to the leading reverse transcriptase inhibitors (RTIs) are established from both in-vitro and in-vivo work, other, rarely reported, resistance mutations may arise occasionally during clinical studies. Isolates with a unique pattern of amino acid substitutions at codons 62, 75, 77, 116, and 115 have been identified in patients receiving prolonged combination therapy with ZDV plus ddI or ddC: these isolates are resistant to both drugs and there is cross-resistance to stavudine and partial cross-resistance to 3TC. No consistent genotypic change has been associated with phenotypic d4T resistance or, indeed, loss of virological effect of this compound.

Mutations to Nucleoside Analogue RT Inhibitors Zidovudine

HIV variants with decreased susceptibility to ZDV were first reported in 1989; in some isolates, greater than 100–fold increases in the concentration of ZDV were required to inhibit viral replication by 50% (Larder B A, Darby G, Richman D D (1989) *Science* 243, 1731–1734). The ZDV-resistant phenotype appears to be reasonably stable in vivo, with resistant virus sometimes being detected up to 1 year after cessation of therapy, (Boucher C A, O'Sullivan E, Mulder J W et al. (1992) *J Infect Disease* 165, 105–110) and despite treatment with didanosine (Smith M S, Koerber K L, Pagano J S, (1994) *J Infect Disease* 169, 184–188).

Nucleotide sequencing of HIV RT has revealed a number of mutations which can influence viral sensitivity to ZDV and which may be used as genotypic markers for the presence of ZDV resistance (Kellam P, Boucher C A B, Tijnagal J M G H et al. (1994) *J Gen Virol* 75, 341–351) (Boucher C A B, Tersmette M, Lange J M A, et al. (1990) *Lancet* 336, 585–590) (Lopez-Galindez C, Rojas J M, Najera R, et al. (1991) *PNAS* 88, 4280–4284). A range of mutants with increasing levels of resistance appear in an ordered manner, with the sequential appearance of these mutations being associated with incremental reductions in viral sensitivity to ZDV (id) (Larder B A, Kellam P, Kemp S D, (1991) *AIDS* 5, 137–144). A substitution at codon 70 (Arg70→Lys) may be transiently dominant and appears critical to virological failure during ZDV monotherapy (DeJong M D, Veenstra J, Stilianakis N I, et al. (1996) *PNAS* 93, 9501–9506). Continued ZDV therapy selects for a further mutation at codon 215, which appears to be a more stable variant, though both Thr215→Tyr and Thr215→Phe substitutions have been described and may coexist (Mayers D L, McCutchan F E, Sanders-Buell E E, et al. (1992) *J Acq Imm Def Synd* 5, 749–759). Virus with additional mutations may then appear, most commonly a substitution at codon 41 (Met41→Leu), followed by further additional mutations at codons 67, (Asp67→Asn) and 219 (Lys219→Gln) or the reappearance of the codon 70 mutation Site-directed mutagenesis techniques have been used to assess the interactions resulting from the different mutations (id). These demonstrated that high-level resistance to ZDV ($IC_{50}$>1 μM) is typically associated with the presence of multiple mutations. Although frequently synergic, mutations may also be antagonistic. For example, a mutation at codon 74 (Leu74→Val) observed during therapy with ddI or ddC has been noted to be antagonistic to the ZDV 215 mutation in vitro, reducing the degree of resistance to ZDV (St Clair M H, Martin J L, Tudor-Williams G, et al. (1991) *Science* 253, 1557–1559). Antagonism of the 215 mutation in vitro has also been reported by the codon 181 mutation selected for by most NNRTIs and the mutation at codon 184 seen with lamivudine and, less frequently, ddC and ddI (Larder B A, (1992) Antimicrob *Agents Chemother* 36, 2064–2669) (Boucher C A B, Cammack N, Schipper P, et al. (1993) *Antimicrob Agents Chemother* 37, 2231–2234) (Tisdale M, Kemp S D, Parry N R, et al. (1993) *PNAS* 90, 5653–5656) (Larder B A, Kemp S D, Harrigan P R (1995) *Science* 269, 696–699) (Zhang D, Caliendo A M, Eron J J, et al. (1994) *Antimicrob Agents Chemother* 38, 282–287). However, novel mutation patterns or additional 'compensatory' mutations may be observed in vivo during combination therapy facilitating dual or multi-drug resistance (see below).

Viral strains resistant to ZDV exhibit cross-resistance to other nucleoside analogues containing the 3'-azido group such as 3'-azido-2',3'-dideoxyuridine (AZU) (Rooke R, Parniak M A, Tremblay M, et al. (1991) *Antimicrob Agents Chermother* 35, 988–991). Cross-resistance to stavudine, a thymidine-based analogue which lacks a 3'-azido moiety, has also been reported by one group in both a laboratory strain of HIV and one of 11 clinical isolates (ibid). Most investigators have found no evidence that mutations selected for during ZDV monotherapy influence sensitivity to ddI, ddC or 3TC (Rooke R, Tremblay M, Soudeyns H, et al. (1989) *AIDS* 3, 411–415) (id) (Larder B A, Chesebro B, Richman D D (1990) *Antimicrob Agents Chemother* 34, 436–441) (id) (Dimitrov D H, Hollinger F B, Baker C J, et al. (1993) *J Infect Disease* 167, 818–823). However, resistance to ddI has been rarely reported after prolonged ZDV therapy (id) (Japour A J, Chatis P A, Eigenrauch H A, et al. (1991) *PNAS* 88, 3092–3096), and one report has suggested that, for each ten-fold decrease in ZDV sensitivity in clinical isolates, there is a corresponding 2.2-fold reduction in susceptibility to ddI and two-fold decrease in sensitivity to ddC (Mayers D L, Japour A J, Arduino J M, et al. (1994) *Antimicrob Agents Chemother* 38, 307–314). Furthermore, patients with ZDV resistance at baseline are significantly less likely to achieve an RNA response after the addition of ddC or ddI than those with wild-type virus at baseline (Holodniy M, Katzenstein D, Mole L, et al. (1996) *J Infect Disease* 174, 854–857).

Zalcitabine And Didanosine

Resistance to ddI is mediated through a Leu74→Val mutation which produces a six-fold to 26-fold reduction in sensitivity, but may partially restore susceptibility to ZDV in vitro by antagonism of the codon 215 mutation. This mutation also reduces sensitivity to ddC by around ten-fold (id). The frequency of the codon 74 mutation has been reported to have increased from zero at the start of therapy to 56% at week 24 in a group of 64 persons with a mean baseline CD4 cell count of 129/mm who switched to ddI having previously received ZDV (Kozal M J, Kroodsma K, Winters M A, et al. (1994) *Annals Intern Med* 121, 263–268). Similarly, in a mixed population of both treatment-naive and ZDV-experienced patients with CD4 cell counts of 200–500/mm who received ddI monotherapy in the ACTG 143 study, 17 of 26 isolates had mutations at codon 74 at 1 year. Mutant codon 74 arose in only two of the 55 patients in this study who received ZDV/ddI combination therapy (Shafer R W, Iversen A K N, Winters M A, et al. (1995) *J Infect Disease* 172, 70–78).

Virus with a mutation at codon 65 (Lys65→Arg) has been isolated from several patients receiving long-term treatment with ddI or ddC. This is associated with a three-fold to five-fold increase in the $IC_{50}$ of ddI with a five-fold to ten-fold reduction in ddC sensitivity and a 20-fold reduction in susceptibility to 3TC (id) (Gu Z, Gao Q, Fang H, et al. (1994) *Antimicrob Agents Chemother* 38, 275–281. A mutation at codon 69 (Thr69→Asp), which leads to a five-fold reduction in sensitivity to ddC but does not appear to result In cross-resistance to other nucleoside analogues, is the most frequent mutation selected for by ddC in vivo (id) (Fitzgibbon J E, Howell R M, Haberzettl C A, et al. (1992) *Antimicrob Agents Chemother* 36, 153–157). The development of resistance to ddC has recently been reviewed elsewhere (Craig C, Moyle G (1997) *AIDS* 11, 271–279).

Combination Therapy–Zidovudine+Zalcitabine or Didanosine

Combination therapy with ZDV/ddC or ZDV/ddI may influence the rate of emergence of resistance and may suppress some of the mutations observed during monotherapy but may result in the appearance of novel (and hence possibly more compromised) mutational patterns.

Novel mutation patterns may emerge during combination therapy. Isolates with a unique pattern of amino acid substitutions at codons 62, 75, 77, 116, and 115 have occasionally been identified in patients receiving prolonged combination therapy with ZDV plus ddI or alternating ZDV/ddC:

these are resistant to both drugs (id) (Shafer R W, Kozal M J, Winters M A, et al. (1994) *J Infect Disease* 169, 722–729) (Shirasaka T, Kavlick M F, Ueno T, et al. (1995) *PNAS* 92, 2398–2402) and confer cross-resistance to stavudine and partial cross-resistance to 3TC. The frequency in persons treated for >1 year with ZDV. ddU ranges from 0 to >10% (ibid). Mutations selected by 3TC (184Val) and nevirapine (181Cys) may readily be added to this background in vitro (Shafer R W, Winters M A, Iversen A K N, et al. (1996) *Antimicrob Agents Chemother* 40, 2887–2890) and 184Val and 103Asp (for loviride resistance) being reported in vivo (Schmit J C, Cogniaux J, Hermans P, et al. (1996) *J Infect Disease* 174, 962–968). While these virus mutations appear to be replication competent in the presence of drug, the likely reason these novel mutations are not seen during monotherapy probably relates to their failure to compete with those mutants that become dominant.

Lamivudine

Resistance to 3TC occurs rapidly in vivo with a substitution at codon 184 (most commonly Met184→Val) (id) (Kuritzkes D R, Quinn J B, Benoit S L, et al. (1996) *AIDS* 10, 975–981) (Bartlett J A, Benoit S L, Johnson V A, et al. (1996) *Annal Intern Med* 125, 161–172) (Eron J J, Benoit S L, Jemsek J, et al. (1995) *NEJM* 333, 1662–1669) (Katlama C, Ingrand D, Loveday C, et al. (1996) *JAMA* 276, 118–125) (Staszewski S, Loveday C, Picazo J J, et al. (1996) *JAMA* 276, 111–117) being observed during both monotherapy and combination therapy and its appearance being temporally associated with at least partial virological failure (id) (Moyle G J (1996) *Drugs* 52, 168–185) (Goulden M G, Cammack N, Hopewell P L, et al. (1996) *AIDS* 10, 101–102). This mutation leads to high-level resistance to 3TC (500-fold to 1000-fold increase in $IC_{50}$), as well as some cross-resistance to both ddI and ddC (four-fold to eight-fold reductions in susceptibility) (id) (Gu Z, Gao Q, Li X, et al. (1992) *J Virol* 66, 7128–7135) In vitro this mutation may antagonize ZDV (id) (id) (id), although dual ZDV/3TC resistance has been reported both in vitro and in clinical isolates (id). Other, possibly compensatory, mutations such as at codon 135 or 333 may be required for dual ZDV/3TC resistance, an issue that is currently under investigation (id). When 3TC was added to patients pre-treated with ZDV in study NUCA3002, phenotypic 3TC resistance developed in 82% of 33 patients by week 12. Of the ten patients with ZDV resistance at baseline (as defined by an $IC_{50}$>0.2 mM) who developed 3TC resistance, four had isolates that were more sensitive to ZDV whilst six patients had dual ZDV/3TC resistance, suggesting that viral resensitization to ZDV is not universal in vivo.

Stavudine

In vitro selection of HIV resistant to d4T, confirmed by site-directed mutagenesis, has identified a mutation at codon 75 (Val75→Thr) which confers a seven-fold increase in $IC_{50}$, as well as reduced susceptibility to both ddI and ddC (Lacey S F, Larder B A (1994) *Antimicrob Agent Chemother* 38, 1428–1432). A mutation at codon 50 leading to a 30-fold reduction in d4T sensitivity, but which does not appear to confer cross-resistance to other nucleoside analogues has also been observed in vitro (Gu Z, Gao Q, Fank H, et al. (1994) *Leukemia* 8, Suppl. 1, 166–169). In vivo, however, a range of amino acid changes, including the codon 75 mutation but not the codon 50 substitution, have been reported. The maximum decrease in sensitivity to d4T seen in 13 ZDV-naive patients followed for 18 to 22 months was 12-fold. However, five patients developed nine-fold to 176-fold reductions in ZDV sensitivity and three subjects developed seven-fold to 29-fold decreases in susceptibility to ddI (Lin P F, Samanta H, Rose R E, et al. (1994) *J Infect Disease* 170, 1157–1164), suggesting use of d4T may limit subsequent therapeutic options in some patients. No consistent mutation pattern for resistance to d4T has, therefore, been established.

Abacavir

In vitro selection of HIV strains resistant to abacavir, confirmed by site-directed mutagenesis, has shown that individual mutations cause only low level resistance to abacavir. Multiple mutations (at least three) are required to produce 10-fold resistance. M184V is the most common resistance mutation selected in vitro in the presence of abacavir and results in a 2–5 fold decrease in susceptibility. Mutations at L74V and F115Y were also shown to contribute to loss of susceptibility to abacavir (Tisdale M, Alnadaf T, Cousens D (1997) Antimicrob Agent Chemother 41, 1094–1098). Cross resistance to ddC and ddI were observed but not to d4T or ZDV. Resistance in HIV derived from patient virus populations has been ascribed to mutations previously associated with NRTI-resistance. A combination of ZDV-resistance mutations (M41L, L210W, T215Y) plus a 3TC-resistance mutation (M184V) showed an eight fold reduction in susceptibility to abacavir. The multi-nucleoside resistance complex (A62V, V75I, F77L, Y116F and Q115M) was associated with a 17 fold reduction in susceptibility (Lanier R, Danehower S, Daluge S, et. al. (1998) $2^{nd}$ International Workshop on HIV Drug Resistance and Treatment Strategies).

Adefovir

In vitro selection in the presence of adefovir resulted in either a K65R or a K70E mutation appearing which confers 16- or 9-fold reduction in susceptibility to adefovir. Studies in patients have reported the appearance of the K70E mutation but not the K65R mutation. Many AZT-resistant, 3TC-resistant and multi-drug resistant viruses remain sensitive to adefovir (Mulato A S, Lamy P D, Miller M D et. al. (1998) *Antimicrob Agent Chemother* 42, 1620–1628).

Clinical Significance of Resistance

Choice of initial and subsequent therapy for HIV infection should be uncompromising in terms of activity but also planned and based rationally on knowledge of resistance and cross-resistance patterns to maintain a wide base of future therapy options.

It is an object of this invention to provide a drug susceptibility and resistance test capable of showing whether a viral population in a patient is resistant to a given prescribed drug. Another object of this invention is to provide a test that will enable the physician to substitute one or more drugs in a therapeutic regimen for a patient that has become resistant to a given drug or drugs after a course of therapy. Yet another object of this invention is to provide a test that will enable selection of an effective drug regimen for the treatment of HIV infections and/or AIDS. Yet another object of this invention is to provide the means for identifying the drugs to which a patient has become resistant, in particular identifying resistance to nucleoside reverse transcriptase inhibitors. Still another object of this invention is to provide a test and methods for evaluating the biological effectiveness of candidate drug compounds that act on specific viruses, viral genes and/or viral proteins particularly with respect to viral drug resistance associated with nucleoside reverse transcriptase inhibitors. It is also an object of this invention to provide the means and compositions for evaluating HIV antiretroviral drug resistance and susceptibility. This and other objects of this invention will be apparent from the specification as a whole.

SUMMARY OF THE INVENTION

The present invention relates to methods of monitoring, using phenotypic and genotypic methods, the clinical progression of human immunodeficiency virus infection and its response to antiviral therapy. The invention is also based, in part, on the discovery that genetic changes in HIV reverse transcriptase (RT) which confer resistance to antiretroviral therapy may be rapidly determined directly from patient plasma HIV RNA using phenotypic or genotypic methods. The methods utilize nucleic acid amplification based assays, such as polymerase chain reaction. Herein after such nucleic acid amplification based assays will be referred to as PCR based assays. Alternatively, methods evaluating viral nucleic acid or viral protein in the absence of an amplification step could utilize the teaching of this invention to monitor and/or modify antiretroviral therapy. This invention is based in part on the discovery of a mutation/insertion at codon 69 either alone or in combination with a mutation at codon 41 and 215 of HIV reverse transcriptase in nucleoside reverse transcriptase inhibitor (NRTI) treated patient(s) in which the presence of the mutations correlate with a decrease in d4T susceptibility, and a decrease in susceptibility to AZT, ddC, ddI, 3TC, and abacavir. The mutations were found in plasma HIV RNA after a period of time following initiation of therapy. The development of the mutation/insertion at codon 69 in addition to the mutation at codon 41 and 215 in HIV RT was found to be an indicator of the development of resistance and ultimately of immunological decline. More specifically the mutation/insertion at codon 69 in RT (T69SSA, T69SSG, T69SSS) may also be associated with mutations associated with resistance to AZT (e.g. M41L, L210W, T215Y) and 3TC (M184V) or ddI/ddC (L74V) which correlate with a decrease in NRTI-susceptibility, including a decrease in d4T susceptibility and a decrease in susceptibility to AZT, ddC, ddI, 3TC and abacavir. It was also found the mutation/insertion at codon 69 in RT (T69SSA, T69SSG, T69SSS) may be associated with mutations associated with resistance to multi-NRTIs at codon 62 (e.g. A62V) and/or a novel mutation at codon 75 (e.g. V75M). It was observed for the first time that the mutation/insertion at codon 69 (T69SSG) and the mutation at codon 75 (V75M) was associated with decreased susceptibility to d4T (three fold) and substantial decreases in AZT susceptibility (thirty fold). This invention is based in part on the discovery of mutations associated with multi-NRTI resistance at codons 62, 75, 77, 116, and 115 of RT discovered to occur in nucleoside reverse transcriptase inhibitor (NRTI) treated patients in which the presence of the mutation correlates with decreased susceptibility to d4T, ddC, ddI and AZT. It has also been discovered that mutations specifically associated with resistance to: AZT at codons 41, 67, 210, 215 and 219 (e.g. M41L, D67N, L210W, T215Y, K219Q); 3TC at codon 184 (M184V); ddC at codon 69 (T69D); or a novel mutatIon at codon 215 (T215V) may accompany the mutations associated with multi-NRTI resistance at codons 62, 75, 77, 116, or 115 which correlate with decreased susceptibility to d4T, ddC, ddI and AZT. This invention is based in part on the discovery of four or more mutations associated with AZT resistance selected from the group consisting of codons 41, 67, 70, 210, 215 and/or 219 (e.g. M41L, D67N, K70R, L210W, T215Y/F, K219Q) either alone or in combination with a mutation at codon 74 (associated with ddI resistance—V74I), 69 (associated with ddC resistance—T69D), 75 (V75M, V75S) and/or 219 (K219N) of HIV reverse transcriptase in nucleoside reverse transcriptase inhibitor treated patient(s) in which the presence of the mutations correlate with a decrease in d4T susceptibility. The mutations were found in plasma HIV RNA after a period of time following initiation of NRTI therapy. It was observed through the construction, by site directed mutagenesis, of resistance test vectors containing the single site mutation at codon 75 (V75I) did not alter d4T susceptibility but increased AZT susceptibility. It was also observed using site directed mutagenesis that the single site mutation at codon 115 (Q151M) reduced d4T and AZT susceptibility. Yet an additional observation of the present invention was that the double site mutation at codons 75 and 115 (V75I+Q151M) reduced d4T and AZT susceptibility. It was also discovered using site directed mutagenesis that resistance test vectors containing five (M41L, D67N, K70R, T215Y, K219Q) or six (M41L, D67N, K70R, L210W, T215Y, K219Q) AZT resistance associated mutations showed reduced susceptibility to d4T and AZT. It was also observed that resistance test vectors containing single site mutations at codons 62, 69 and 75 (A62V, T69SSA, V75I, V75V) did not reduce d4T susceptibility. However, it was observed that the single site mutation at codon 75 (V75I) or (V75V) increased AZT susceptibility slightly. The T69SSA single site mutation reduced AZT susceptibility slightly while the A62V mutation had no effect on AZT susceptibility. In yet further studies using site directed mutagenesis, it was observed that resistance test vectors containing double site mutations at codons 62 and 69 (e.g. A62V+T69SSA) did not reduce d4T susceptibility more than the T69SSA mutation alone, but further reduce AZT susceptibility due to the T69SSA mutation alone. In still further studies using site directed mutagenesis, it was observed that resistance test vectors containing double site mutations at codons 62 and 75 (e.g. A62V+V75I) had no effect on d4T susceptibilIty. It was also found that the A62V mutation did not alter the reduced AZT susceptibility caused by the V75I mutation. In yet further studies using site directed mutagenesis, it was observed that a combination of three mutations at codons 62, 69 and 75 (e.g. A62V+T69SSA+V75I) did not reduce d4T susceptibility more than the T69SSA mutation alone. It was also observed in the case of the combination of three mutations at codons 62, 69 and 75 (e.g. A62V+T69SSA+V75I) that the V75I mutation completely suppressed the reduced AZT susceptibility caused by the combination of A62V and T69SSA mutations. In still further studies using site directed mutagenesis, it was observed that resistance test vectors containing three mutations at codons 41, 69 and 215 (e.g. M41L+T69SSA+T215Y) showed a significant decrease in both d4T and AZT susceptibility. In yet further studies using site directed mutagenesis, it was observed that a combination of four mutations at codons 41, 62, 69 and 215 (e.g. M41L+A62V+T69SSA+T215Y) did reduce d4T susceptibility more than the T69SSA mutation alone or the T69SSA+A62V double mutant. It was also observed in the case of the combination of four mutations at codons 41, 62, 69 and 215 (e.g. M41L+A62V+T69SSA+T215Y) that the combination of all four mutations reduced AZT susceptibility more than the combination of M41L and T215Y mutations alone. In yet further studies using site directed mutagenesis, it was observed that a combination of five mutations at codons 41, 62, 69, 184 and 215 (e.g. M41L+A62V+T69SSA+M184V+T215Y) did reduce d4T susceptibility more than the T69SSA mutation alone or the A62V+T69SSA double mutant. It was also observed in the case of the combination of five mutations at codons 41, 62, 69, 184 and 215 (e.g. T41L+A62V+T69SSA+M184V+T215Y) that the M184V mutation suppressed the reduced AZT susceptibility caused by the combination of M41L, A62V, T69SSA and T215Y mutations. In yet another study using site directed mutagenesis the T69SSA mutation in a clone of a patient's virus was reverted (T69SSA→SSA69T). Reversion of the T69SSA mutation reduced d4T resistance (i.e.

increased susceptibility) and also reduced AZT resistance (i.e. increased susceptibility).

In yet further studies using site directed mutagenesis, it was observed that the introduction of the L210W mutation with mutations at 41, 69, and 215 (e.g. M41L+T69SSA+ T215Y) resulted in a substantial decrease in susceptibility to AZT compared to the 140-fold decrease in susceptibility observed for AZT without the 210 mutation. In still further studies using site directed mutagenesis, it was observed that four mutations at codons 41, 62, 69 and 215 (e.g. M41L+ A62V+T69SSA+T215Y) showed a substantial decrease in AZT susceptibility (greater than 1000-fold) and only slight decreases in susceptibility to the other NRTIs. In yet further studies using site directed mutagenesis, it was observed that the introduction of the L210W mutation with four mutations at codons 41, 62, 69 and 215 (e.g. M41L+A62V+T69SSA+ T215Y) had little effect on drug susceptibility and showed a resistance profile similar to the profile obtained for when only the four mutations were present. In yet further studies using site directed mutagenesis, it was observed that the introduction of the T215Y mutation with mutations at 62 and 69 (e.g. A62V+T69SSA) resulted in a substantial decrease in susceptibility to AZT (greater than 1000-fold) compared to the 7-fold decrease in susceptibility observed for AZT without the 215 mutation. It was also observed that the introduction of the L74V mutation with mutations at 62 and 69 (e.g. A62V+T69SSA) resulted in a shift back to wild-type susceptibility for AZT. In yet further studies using site directed mutagenesis, it was observed that the introduction of the V75M mutation with four mutations at codons 41, 69, 210 and 215 (e.g. M41L+T69SSA+L210W+T215Y) had little effect on drug susceptibility and showed a resistance profile similar to the profile obtained when only the four mutations were present.

In a further embodiment of the invention, PCR based assays, including phenotypic and genotypic assays, may be used to detect mutations at codon 69 in combination with mutations at other codons including 41 and/or 215 of HIV RT which correlate with a specific pattern of resistance to antiretroviral therapies and subsequent immunologic decline. More specifically in yet another embodiment of the invention PCR based assays, including phenotypic and genotypic assays, may be used to detect mutations at codon 69 (T69SSA, T69SSG, T69SSS) in combination with mutations at other codons including 41 (M41L), 210 (L210W), 215 (T215Y), 184 (M184V) and/or 74 (L74V) of HIV RT which correlate, as described herein, with a specific pattern of resistance to antiretroviral therapies and subsequent immunologic decline. In yet another embodiment of the invention, PCR based assays, including phenotypic and genotypic assays, may be used to detect mutations at codon 62, 75, 77, 116 or 115 either alone or in combination with mutations at other codons including 41, 67, 210, 215, 219, 184, 69 and/or 215 of HIV HT which correlate, as described herein, with resistance to antiretroviral therapies and immunologic decline. Examples of the mutations at the aforementioned codons include, but are not limited to (A62V, V75I, F77L, F116Y, Q151M) and (M41L, D67N, L210W, T215Y, K219Q, M184V/I, T69D, T215Y). In yet another embodiment of the invention, PCR based assays, including phenotypic and genotypic assays, may be used to detect four or more mutations in RT at codons in the group consisting of 41, 67, 70, 210, 215 and/or 219 (e.g. M41L, D67N, K70R, L210W, T215Y/F, K219Q) either alone or in combination with mutation at codon 74 (V74I), 69 (T69D), 75 (V75M, V75S) and/or 219 (K219N) of HIV RT which correlates, as described herein, with resistance to antiretroviral therapy and immunologic decline. Once mutations at codon 69 either alone or in combination with mutation at codon 41 and 215 of HIV RT in a patient undergoing NRTI antiretroviral therapy, an alteration in the therapeutic regimen must be considered. Similarly, once mutations at codon 69 and/or 41, 210, 215, 184 and/or 74 have been detected in a patient undergoing certain NRTI antiretroviral therapy, an alteration in the therapeutic regimen must be considered. Similarly, once mutations at codon 62, 75, 77, 116 and/or 115 either alone or in combination with mutations associated with resistance to AZT, 3TC, ddC or a mutation T215V has been detected in a patient undergoing certain NRTI antiretroviral therapy, an alteration in the therapeutic regimen must be considered. Similarly, once four or more mutations associated with AZT resistance selected from the group consisting of 41, 67, 70, 210, 215 and/or 219 either alone or in combination with a mutation at codon 74 (V74I), 69 (T69D), 75 (V75M, V75S) and/or 219(K219N) has been detected in a patient undergoing certain NRTI antiretroviral therapy, an alteration in the therapeutic regimen must be considered. PCR based assays, including phenotypic and genotypic assays, may be used to detect mutations at codon 69 in combination with mutations at other codons including 41 and/or 215 of HIV RT which correlate with a specific pattern of resistance to antiretroviral therapies and subsequent immunologic decline. Similarly, PCR based assays, including phenotypic and genotypic assays, may be used to detect mutations at codon 69 in combination with mutations at other codons including 41, 219, 215, 184 and/or 74 of HIV RT which correlate with a specific pattern of resistance to antiretroviral therapies and subsequent immunologic decline. PCR based assays, including phenotypic and genotypic assays, may be used to detect mutations at codon 69 in combination with mutations at other codons including 62 and/or 75 of HIV RT which correlate with a specific pattern of resistance to antiretroviral therapies and subsequent immunologic decline. PCR based assays, including phenotypic and genotypic assays, may be used to detect mutations at codon 62, 75, 77, 116 and 115 either alone or in combination with mutations at other codons including 41, 67, 210, 215, 219, 184, 69 and/or T215V of HIV RT which correlate with a specific pattern of resistance to antiretroviral therapies and subsequent immunologic decline. The timing at which a modification of the therapeutic regimen should be made, following the assessment of the antiretroviral therapy using PCR based assays, may depend on several factors including the patient's viral load, CD4 count, and prior treatment history.

In another aspect of the invention there is provided a method for assessing the effectiveness of a nucleoside reverse transcriptase antiretroviral drug comprising: (a) introducing a resistance test vector comprising a patient-derived segment and an indicator gene into a host cell; (b) culturing the host cell from step (a); (c) measuring expression of the indicator gene in a target host cell wherein expression of the indicator gene is dependent upon the patient derived segment; and (d) comparing the expression of the indicator gene from step (c) with the expression of the indicator gene measured when steps (a)–(c) are carried out in the absence of the NRTI anti-HIV drug, wherein a test concentration of the NRTI, anti-HIV drug is presented at steps (a)–(c); at steps (b)–(c); or at step (c).

This invention also provides a method for assessing the effectiveness of non-nucleoside reverse transcriptase antiretroviral therapy in a patient comprising: (a) developing a standard curve of drug susceptibility for an NRTI anti-HIV drug; (b) determining NRTI anti-HIV drug susceptibility in the patient using the susceptibility test described above; and (c) comparing the NRTI anti-HIV drug susceptibility in step (b) with the standard curve determined in step (a), wherein a decrease in NRTI anti-HIV susceptibility indicates development of anti-HIV drug resistance in the patient.

This invention also provides a method for evaluating the biological effectiveness of a candidate HIV antiretroviral drug compound comprising: (a) introducing a resistance test vector comprising a patient-derived segment and an indicator gene into a host cell; (b) culturing the host cell from step (a); (c) measuring expression of the indicator gene in a target host cell wherein expression of the indicator gene is dependent upon the patient derived segment; and (d) comparing the expression of the indicator gene from step (c) with the expression of the indicator gene measured when steps (a)–(c) are carried out in the absence of the candidate anti-viral drug compound, wherein a test concentration of the candidate anti-viral drug compound is present at steps (a)–(c); at steps (b)–(c); or at step (c)

The expression of the indicator gene in the resistance test vector in the target cell is ultimately dependent upon the action of the patient-derived segment sequences. The indicator gene may be functional or non-functional.

In another aspect this invention is directed to antiretroviral drug susceptibility and resistance tests for HIV/AIDS. Particular resistance test vectors of the invention for use in the HIV/AIDS antiretroviral drug susceptibility and resistance test are identified.

In yet another aspect this invention provides for the identification and assessment of the biological effectiveness of potential therapeutic antiretrovlral compounds for the treatment of HIV and/or AIDS. In another aspect, the invention is directed to a novel resistance test vector comprising a patient-derived segment further comprising one or more mutations on the RT gene and an indicator gene.

Figure 1:
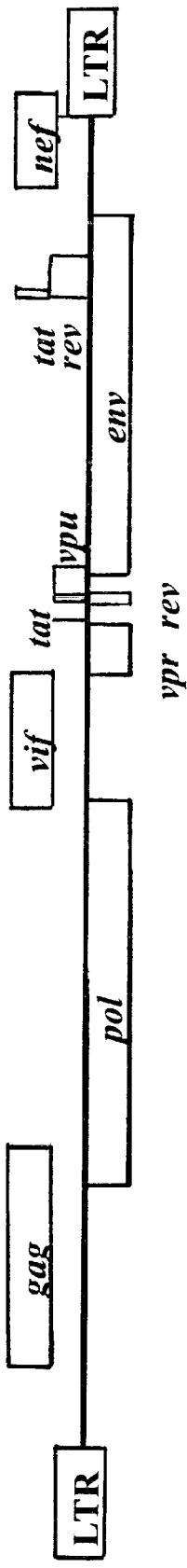
FIG. 1
Figure 1:
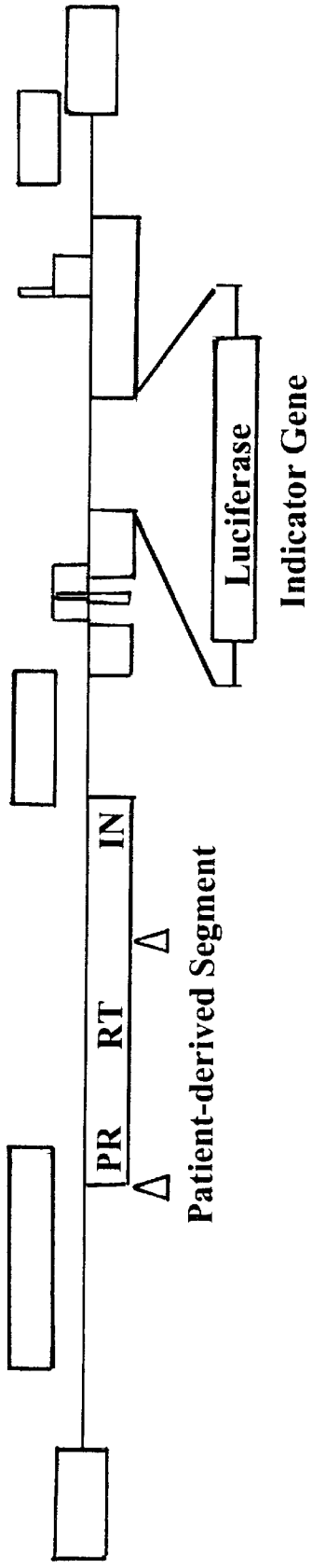
Figure 2:
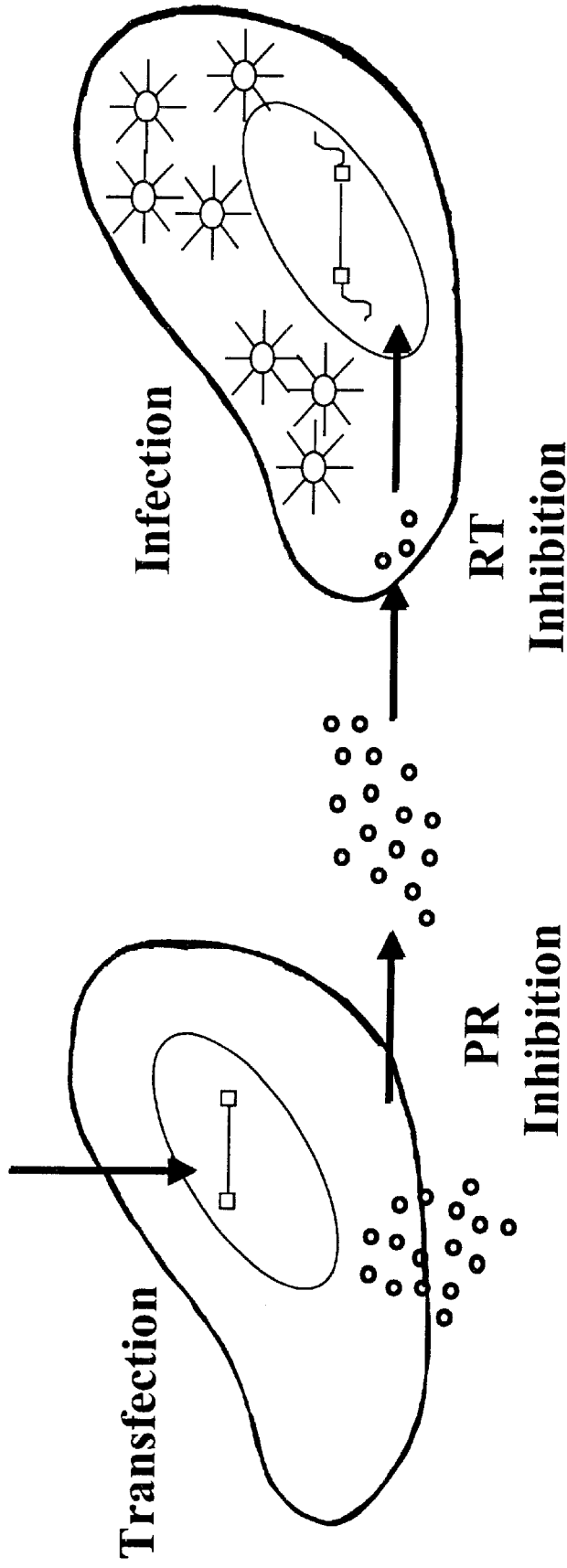

Resistance Test Vector. A diagrammatic representation of the resistance test vector comprising a patient derived segment and an indicator gene.

FIG. 2

Two Cell Assay. Schematic Representation of the Assay. A resistance test vector is generated by cloning the patient-derived segment into an indicator gene viral vector. The resistance test vector is then co-transfected with an expression vector that produces amphotropic murine leukemia virus (MLV) envelope protein or other viral or cellular proteins which enable infection. Pseudotyped viral particles are produced containing the protease (PR) and the reverse transcriptase (RT) gene products encoded by the patient-derived sequences. The particles are then harvested and used to infect fresh cells. Using defective PR and RT sequences it was shown that luciferase activity is dependent on functional PR and RT. PR inhibitors are added to the cells following transfection and are thus present during particle maturation. RT inhibitors, on the other hand, are added to the cells at the time of or prior to viral particle infection. The assay is performed in the absence of drug and in the presence of drug over a wide range of concentrations. The amount of luciferase is determined and the percentage (%) inhibition is calculated at the different drug concentrations tested.

FIG. 3

Examples of phenotypic drug susceptibility profiles. Data are analyzed by plotting the percent inhibition of luciferase activity vs. log concentration. This plot is used to calculate the drug concentration that is required to inhibit virus replication by 50% ($IC_{50}$) or by 95% ($IC_{95}$). Shifts in the inhibition curves towards higher drug concentrations are interpreted as evidence of drug resistance. Three typical curves for a nucleoside reverse transcriptase inhibitor (AZT), a non-nucleoside reverse transcriptase inhibitor (delavirdine), and a protease inhibitor (ritonavir) are shown. A reduction in drug susceptibility (resistance) is reflected in a shift in the drug susceptibility curve toward higher drug concentrations (to the right) as compared to a baseline (pre-treatment) sample or a drug susceptible virus control, such as PNL4-3 or HXB-2, when a baseline sample is not available.

FIG. 4 d4T Resistant Patient Isolates: Multi-NRTI Resistance Mutations. These four viruses exhibit reduced susceptibility to d4T (4–12 fold) and contain RT mutations associated with multi-NRTI resistance (A62V, V75I, F77L, F116Y, Q151M). Some viruses also contain mutations specifically associated with resistance to AZT (M41L, D67N, L210W, T215Y, K219Q), 3TC (M184V/I), or ddC (T69D), or a previously undescribed mutatIon (T215V). Mutations for the test virus are listed below the test virus profile. Mutations within parentheses indicate that the virus population was comprised of a mixture of wildtype and mutant. Genotype described here is partial. For a complete description of the patient genotype, see example 3.

FIG. 5 d4T Resistant Patient Isolates: T69SSX Mutations/ Insertions. These four viruses exhibit reduced susceptibility to d4T (2–10 fold) and contain previously undescribed mutations/insertions in RT (T69SSA, T69SSG, T69SSS). These viruses also contain mutations associated with resistance to AZT (M41L, L210W, T215Y) and 3TC (M184V/I) or ddI/ddC (L74V). Some viruses also contain a mutation associated with resistance to multi-NRTIs (A62V) and/or a previously undescribed mutation (V75M). Mutations for the test virus are listed below the test virus profile. Mutations within parentheses indicate that the virus population was comprised of a mixture of wildtype and mutant. Genotype described here is partial. For a complete description of the patient genotype, see example 4.

FIG. 6 d4T Resistant Patient Isolates: AZT Resistance-Associated Mutations. These four viruses exhibit reduced susceptibility to d4T (3–6 fold) and contain 4 or more mutations associated AZT resistance (M41L, D67N, K70R, L210W, T215Y/F, K219Q). Some viruses also contained mutations associated with resistance to ddI (V74I), ddC (T69D), or previously undescribed mutations (V75M, V75S, K219N). Mutations for the test virus are listed below the test virus profile. Genotype described here is partial. For a complete description of the patient genotype, see example 5.

FIG. 7

Site Directed Mutations: Multi-NRTI Resistance-Associated Mutations. Resistance test vectors containing single site (V75I), (Q151M) and double site (V75I+Q151M) mutations were constructed by site directed mutagenesis. Phenotypic susceptibility to d4T and AZT of resistance test vectors containing these site directed mutations are shown. Left panel: The Q151M mutation reduced d4T susceptibility approximately three-fold. The V75I mutation did not alter d4T susceptibility. Right panel: The Q151M mutation reduced AZT susceptibility approximately five-fold. The V75I mutation increased AZT susceptibility approximately two-fold.

FIG. 8

Site Directed Mutations: AZT Resistance-Associated Mutations. Resistance test vectors containing five (M41L, D67N, K70R, T215Y, K219Q) or six (M41L, D67N, K70R, L210W, T215Y, K219Q) AZT resistance associated mutations were constructed by site directed mutagenesis. Phenotypic susceptibility to d4T and AZT of resistance test vectors containing these site directed mutations are shown. Left panel: Resistance test vectors containing five or six AZT resistance-associated mutations were approximately two-fold less susceptible to d4T than the control resistance test vector. Right panel: Resistance test vectors containing five or six AZT resistance-associated mutations were approximately 75–180-fold less susceptible to AZT than the control resistance test vector.

FIG. 9

Site Directed Mutations: Single Mutations at RT Amino Acids 62, 69, and 75. Resistance test vectors containing single site (A62V, T69SSA, V75I, V75V) mutations were constructed by site directed mutagenesis. Phenotypic susceptibility to d4T and AZT of resistance test vectors containing these site directed mutations are shown. Left panel: The T69SSA and V75V mutations did not reduce d4T susceptibility appreciably (less than two-fold). The A62V and V75I mutations had no affect on d4T susceptibility. Right panel: The V75I and V75V mutations increased AZT susceptibility slightly (approximately two-fold). The T69SSA mutation reduced AZT susceptibility slightly (approximately two-fold) The A62V mutation had no affect on AZT susceptibility.

FIG. 10

Site Directed Mutations: Multiple Mutations at RT Amino Acids 62, 69, and 75. Resistance test vectors containing double site (A62V+T69SSA) (A62V+V75I) and triple site (A62V+T69SSA+V75I) mutations were constructed by site directed mutagenesis. Phenotypic susceptibility to d4T and AZT of resistance test vectors containing these site directed mutations are shown. Left panels: A combination of the A62V and T69SSA mutations did not reduce d4T susceptibility more than the T69SSA mutation alone. However, these two mutations reduced AZT susceptibility by approximately six-fold. Center panels: A combination of the A62V and V75I mutations had no affect on d4T susceptibility. The A62V mutation did not alter the reduced level of AZT susceptibility caused by the V75I mutation. Right panels: A combination of the A62V, T69SSA, and V75I mutations did not reduce d4T susceptibility more than the T69SSA mutation alone. The V75I mutation completely suppressed the six-fold AZT resistance caused by the combination of A62V and T69SSA mutations.

FIG. 11

Patient 285 clones: T69SSA Site Directed Revertant. Site directed mutagenesis was used to revert the T69SSA mutation in a molecular clone of a resistance test vector prepared from patient sample 285. The phenotypic susceptibility to d4T and AZT of the parental clone (T69SSA) and the revertant clone (SSA69T) are shown. Left panel: Reversion of the T69SSA mutation reduced d4T resistance by approximately three-fold. Right panel: Reversion of the T69SSA mutation reduced AZT resistance by approximately thirty-fold.

FIG. 12

Patient 770 Clones: +/−T69SSG+V75M. The resistance test vector pool derived from patient sample 770 was heterogeneous consisting of variants with or without the T69SSG and V75M mutations. The phenotypic susceptibility to d4T and AZT of resistance test vectors with or without these mutations are shown. Left panel: Resistance test vector clones containing the T69SSG and V75M mutations were more than three-fold more resistant to d4T than clones without these mutations. Right panel: Resistance test vector clones containing the T69SSG and V75M mutations were approximately thirty-fold more resistant to AZT than clones without these mutations.

FIG. 13

Site Directed Mutations: Multiple Mutations at RT Amino Acids 41, 62, 69, 184 and 215. Resistance test vectors containing three (M41L+T69SSA+T215Y) four (M41L+A62V+T69SSA+T215Y) or five (M41L+A62V+T69SSA+M184V+T215Y) mutations were constructed by site directed mutagenesis. Phenotypic susceptibility to a panel of 6 NRTIs (AZT, ddC, DDI, 3TC, d4T and abacavir) of resistance test vectors containing these site directed mutations are shown. The M41L+T69SSA+T215Y significantly reduced susceptibillty to all of the NRTIs tested (2–150 fold). The addition of A62V resulted in a further reduction in susceptibility to AZT, d4T and ddI but had no effect on susceptibility to 3TC, ddC and abacavir. A resistance test vector with M41L+A62V+T69SSA+M184V+T215Y was more susceptible to AZT, d4T and ddI than the resistance test vector with the 4 mutations M41L+A62V+T69SSA+T215Y. The addition of M184V led to decreased susceptibility to 3TC but had no effect on susceptibility to ddC or abacavir.

DETAILED DESCRIPTION OF THE INVENTION

The present invention relates to methods of monitoring the clinical progression of HIV infection in patients receiving antiretroviral therapy, particularly nucleoside reverse transcriptase inhibitor antiretroviral therapy.

In one embodiment, the present invention provides for a method of assessing the effectiveness of antiretroviral therapy of a patient comprising (i) collecting a biological sample from an HIV-infected patient; and (ii) determining whether the biological sample comprises nucleic acid encoding HIV RT having a mutation at one or more positions in the RT. The mutation(s) correlate positively with alterations in phenotypic susceptibility/resistance. In a specific embodiment, the invention provides for a method of assessing the effectiveness of NRTI antiretroviral therapy of a patient comprising (i) collecting a biological sample from an HIV-infected patient; and (ii) determining whether the biological sample comprises nucleic acid encoding HIV RT having a mutation at codon 69. This invention established, using a phenotypic susceptibility assay, that mutations at codon 69 either alone or in combination with a mutation at codon 41 and 215 of HIV reverse transcriptase are correlated with a decrease in d4T susceptibility. In another specific embodiment, the invention provides for a method of evaluating the effectiveness of NRTI antiretroviral therapy of a patient comprising (i) collecting a biological sample from an HIV-infected patient; and (ii) determining whether the biological sample comprises nucleic acid encoding HIV RT having one or more mutation(s) at codon(s) selected from the group consisting of 62, 75, 77, 116 and/or 115. This invention established, using a phenotypic susceptibility assay, that mutations at codons selected from the group consisting of 62, 75, 77, 116 and/or 115 either alone or in combination with one or more mutation(s) at codons selected from the group consisting of 41, 67, 210, 215, 219, 184, 69 and/or T215V of HIV reverse transcriptase are correlated with a decrease in d4T susceptibility (increased resistance). Under the foregoing circumstances, the phenotypic susceptibility/resistance profile and genotypic profile of the HIV virus infecting the patient has been altered reflecting some change in the response to the antiretroviral agent. In the case of NRTI antiretroviral therapy, the HIV virus infecting the patient may be resistant to one or more but not another of the NRTIs as described herein. It therefore may be desirable after detecting the mutation, to either increase the dosage of the antiretroviral agent, change to another antiretroviral agent, or add one or more additional antiretroviral agents to the patient's therapeutic regimen. For example, if the patient was being treated with stavudine (d4T) when the 62, 75, 77, 116 and/or 115 mutation either alone or in combination with one or more mutation(s) at codons selected from the group consisting of 41, 67, 210, 215, 219, 184, 69 and/or T215V arose, the patient's therapeutic regimen may desirably be altered by either (i) changing to a different NRTI antiretroviral agent and stopping d4T treatment; or (ii) increasing the dosage of d4T; or (iii) adding another antiretroviral agent to the patient's therapeutic regimen. The effectiveness of the modification in therapy may be evaluated by monitoring viral burden such as by HIV RNA copy number. A decrease in HIV RNA copy number correlates positively with the effectiveness of a treatment regimen. The phrase "correlates positively," as used herein, indicates that a particular result renders a particular conclusion more likely than other conclusions.

Another preferred, non-limiting, specific embodiment of the invention is as follows: A method of assessing the effectiveness of NRTI therapy of a patient comprising (i) collecting a biological sample from an HIV-infected patient; (ii) amplifying the HIV-encoding RNA in the biological sample by converting the RNA to cDNA and amplifying HIV sequences using HIV primers that result in a PCR product that comprises the RT gene; (iii) performing PCR using primers that result in PCR products comprising wild type or mutant 69 and 41 and 215 codons; and (iv) determining, via the products of PCR, the presence or absence of a mutation at codon 69 or 41 or 215 or all three. Yet another preferred, non-limiting specific embodiment, of the invention is as follows: A method of assessing the effectiveness of NRTI therapy of a patient comprising (i) collecting a plasma sample from an HIV-infected patient; (ii) amplifying the HIV-encoding RNA in the plasma sample by converting the RNA to cDNA and amplifying HIV sequences using HIV primers that result in a PCR product that comprises the RT gene; (iii) performing PCR using primers that result in PCR products comprising the wild type or mutations at codons selected from the group consisting of 62, 75, 77, 116 and 115 and/or one or more mutation(s) at codons selected from the group consisting of 41, 67, 210, 215, 219, 184, 69; and (iv) determining, via the products of PCR, the presence or absence of a mutation at codon 62, 75, 77, 116 and 115 and/or one or more mutation(s) at codons selected from the group consisting of 41, 67, 210, 215, 219, 184, 69. Yet another preferred, non-limiting specific embodiment, of the invention is as follows: A method of assessing the effectiveness of NRTI therapy of a patient comprising (i) collecting a plasma sample from an HIV-infected patient; (ii) amplifying the HIV-encoding RNA in the plasma sample by converting the RNA to cDNA and amplifying HIV sequences using HIV primers that result in a PCR product that comprises the RT gene; (iii) performing PCR using primers that result in PCR products comprising the wild type or mutations at codon 69 and 41, 219, 215, 184 or 74; and (iv) determining, via the products of PCR, the presence or absence of a mutation at codon 69 (T69SSA, T69SSG, T69SSS) and 41 (M41L), 210 (L210W), 215 (T215Y), 184 (M184V) or 74 (L74V). Yet another preferred, non-limiting specific embodiment, of the invention is as follows: A method of assessing the effectiveness of NRTI therapy of a patient comprising (i) collecting a plasma sample from an HIV-infected patient; (ii) amplifying the HIV-encoding RNA in the plasma sample by converting the RNA to cDNA and amplifying HIV sequences using HIV primers that result in a PCR product that comprises the RT gene; (iii) performing PCR using primers that result in PCR products comprising the wild type or mutations at codon 41, 67, 70, 210, 215 and 219; and (iv) determining, via the products of PCR, the presence or absence of a mutation at codon 41 (m41L), 67 (D67N), 70 (K70R); 210 (L210W), 215 (T215Y/F), and 219 (K219Q).

The presence of the mutation at codon 69 and 41 and 215 of HIV RT indicates that the effectiveness of the current or prospective NRTI therapy may require alteration, since as shown by this invention mutation at codon 69 reduces d4T susceptibility. Using the methods of this invention change in the NRTI therapy would be indicated. Similarly, using the means and methods of this invention the presence of the mutation at codon(s) 62, 75, 77, 116 and/or 115 of the HIV RT indicates that the effectiveness of the current or prospective NRTI therapy may require alteration, since as shown by this invention mutation at codons 62, 75, 77, 116 and/or 115 reduces d4T susceptibility. Similarly, using the means and methods of this invention the presence of the mutation/insertion at codon 69 (T69SSA, T69SSG, T69SSS) and 41 (M41L), 210/L210W), 215 (T215Y), 184 (M184V) or 74 (L74V) of the HIV RT indicates that the effectiveness of the current or prospective NRTI therapy may require alteration, since as shown by this invention mutation/insertion at codon 69 either alone or in combination with mutation at codons 41, 210, 215, 184 or 74 reduces d4T susceptibility.

Another preferred, non-limiting, specific embodiment of the invention is as follows: a method of evaluating the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at four or more codon(s) selected from the group consisting of 41, 67, 70, 210, 215 and 219 either alone or in combination with mutations at codon(s) 74 (V74I), 69 (T69D), 75 (V75M, V75S) or 219 (K219N). Using the phenotypic susceptibility assay, it was observed that the presence of the four or more mutations correlates positively with reduced d4T susceptibility. Using the phenotypic susceptibility assay, it was observed that the presence of the four or more mutations correlates positively with d4T resistance. In another embodiment, the mutated codon 41, 67, 70, 210, 215 and 219 of HIV RT encode 41L, 67N, 70R, 210W, 215Y/F and 219Q. In a further embodiment, the reverse transcriptase has a mutation at codon V74T, T69D, V75M, V25S, K219N, or a combination thereof in addition to the four or more mutations at codons 41, 67, 70, 210, 215 and 219 of HIV RT.

Another preferred, non-limiting, specific embodiment of the invention is as follows: a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at one or more codons selected from the group consisting of 67, 75, 77, 116 and 115 and either alone or in combination with mutation at one or more codon(s) selected from the group consisting of (E6D, K20R, A33I, T39A, E44D, S68G, Y115F, I167V, E138A, G196A, I202V, T215V, D218E, and T240K). Using the phenotypic susceptibility assay, it was observed that the presence of the mutations at codons 62, 75, 77, 116 and 115 alone or in combination with one or more mutations at codon(s) 62, 75, 77, 116 and 115 of HIV RT cause a decrease in d4T susceptibility.

This invention provides a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation/insertion at codon 69 (T69SSA, T69SSG, T69SSS) either alone or in combination with mutations at one or more codons selected from the group consisting of V75M, A158S, K20R, V21I, K102M, V179I, V241L, I283I, E297R, E6D, Q174R, D177E, R284K, A288S, E291D. Using the phenotypic susceptibility assay it was observed that the presence of mutation/insertion at codon 69 correlates positively with a decrease in d4T susceptibility.

This invention provides a method of assessing the effectiveness of antiretroviral therapy of an HIV-infected patient comprising: (a) collecting a biological sample from an HIV-infected patient; and (b) determining whether the biological sample comprises nucleic acid encoding HIV reverse transcriptase having a mutation at four or more codons selected from the group consisting of 41, 67, 70, 210, 215 and 219 either alone or in combination with mutations at one or more codons selected from the group consisting of P1L, P9R, K20R, T39D, K43E, E44D, K64Y, V75M/S, G99R, L109V, V118I, K173E/T, I202T, R211H/T, D218E, K219N, H221Y, L228H, L283I, R284K, and A288T. Using the phenotypic susceptibility assay it was observed that the presence of mutations at four or more codons selected from the group consisting of 41, 67, 70, 210, 215 and 219 can correlate positively with a decrease in d4T susceptibility.

This invention also provides the means and methods to use the resistance test vector comprising an HIV gene further comprising an NRTI mutation for drug screening. More particularly, the invention describes the resistance test vector comprising the HIV reverse transcriptase having mutations at codons 69 and 41 and 215 for drug screening. The invention also describes the resistance test vector comprising the HIV reverse transcriptase having mutations at codons selected from the group consisting of 62, 75, 77, 116 and 115 and/or 41, 67, 70, 210, 215 and 219. The invention also describes the resistance test vector comprising the HIV reverse transcriptase having mutations at four or more codons selected from the group consisting of 41, 67, 70, 210, 215 and 219. The invention further relates to novel vectors, host cells and compositions for isolation and identification of the nucleoside HIV-1 reverse transcriptase inhibitor resistance mutant and using such vectors, host cells and compositions to carry out anti-viral drug screening. This invention also relates to the screening of candidate drugs for their capacity to inhibit said mutant.

This invention provides a method for identifying a compound which is capable of affecting the function of the reverse transcriptase of HIV-1 comprising contacting the compound with the polypeptide(s) comprising all or part of the HIV-1 reverse transcriptase, wherein codon 69 is changed to code for the insertion of amino acid residues SSS, SSG or SSA in place of threonine, wherein a positive binding indicates that the compound is capable of affecting the function of said reverse transcriptase.

This invention provides a method for identifying a compound which is capable of affecting the function of HIV-1 reverse transcriptase comprising contacting the compound with a polypeptide(s) comprising all or part of the HIV-1 reverse transcriptase, wherein one or more codons selected from the group consisting of 62, 75, 77, 116 and 115 is changed to code for an amino acid residue(s) other than alanine, valine, phenylaianine, phenylalanine and glutamine respectively, wherein a positive binding indicates that the compound is capable of affecting the function of said reverse transcriptase.

This invention also provides a method for identifying a compound which is capable of affecting the function of the reverse transcriptase of HIV-1 comprising contacting the compound with a polypeptide comprising a portion of the reverse transcriptase of HIV--1, wherein four or more codons selected from the group consisting of 41, 67, 70, 210, 215 and 219 are changed to code for an amino acid residues other than methionine, aspartic acid, lysine, leucine, threonine or lysine respectively, wherein a positive binding indicates that the compound is capable of affecting the function of said reverse transcriptase.

As used herein, "patient-derived segment" encompasses segments derived from human and various animal species. Such species include, but are not limited to chimpanzees, horses, cattles, cats and dogs.

Patient-derived segments can also be incorporated into resistance test vectors using any of several alternative cloning techniques as set forth in detail in PCT International Application No. PCT/US97/01609, filed Jan. 29, 1997 which is hereby incorporated by reference. For example, cloning via the introduction of class II restriction sites into both the plasmid backbone and the patent-derived segments or by uracil DNA glycosylase primer cloning.

The patient-derived segment may be obtained by any method of molecular cloning or gene amplification, or modifications thereof, by introducing patient sequence acceptor sites, as described below, at the ends of the patient-derived segment to be introduced into the resistance test vector. For example, in a gene amplification method such as PCR, restriction sites corresponding to the patient-sequence acceptor sites can be incorporated at the ends of the primers used in the PCR reaction. Similarly, in a molecular cloning method such as cDNA cloning, said restriction sites can be incorporated at the ends of the primers used for first or second strand cDNA synthesis, or in a method such as primer-repair of DNA, whether cloned or uncloned DNA, said restriction sites can be incorporated into the primers used for the repair reaction. The patient sequence acceptor sites and primers are designed to improve the representation of patient-derived segments. Sets of resistance test vectors having designed patient sequence acceptor sites provide representation of patient-derived segments that may be underrepresented in one resistance test vector alone.

"Resistance test vector" means one or more vectors which taken together contain DNA or RNA comprising a patient-derived segment and an indicator gene. Resistance test vectors are prepared as described in PCT International Application No. PCT/US97/01609, filed Jan. 29, 1997 which is hereby incorporated by reference, by introducing patient sequence acceptor sites, amplifying or cloning patient-derived segments and inserting the amplified or cloned sequences precisely into indicator gene viral vectors at the patient sequence acceptor sites. Alternatively, a resistance test vector (also referred to as a resistance test vector system) is prepared by introducIng patient sequence acceptor sites into a packaging vector, amplifying or cloning patient-derived segments and inserting the amplified or cloned sequences precisely into the packaging vector at the patient sequence acceptor sites and co-transfecting this packaging vector with an indicator gene viral vector.

"Indicator or indicator gene," as described in PCT International Application No. PCT/US97/01609, filed Jan. 29, 1997 refers to a nucleic acid encoding a protein, DNA or RNA structure that either directly or through a reaction gives rise to a measurable or noticeable aspect, e.g. a color or light of a measurable wavelength or in the case of DNA or RNA used as an indicator a change or generation of a specific DNA or RNA structure. Preferred examples of an indicator gene is the E. coli lacZ gene which encodes beta-galactosidase, the luc gene which encodes luciferase either from, for example, Photonis pyralis (the firefly) or Renilla reniformis (the sea pansy), the E. coli phoA gene which encodes alkaline phosphatase, green fluorescent protein and the bacterial CAT gene which encodes chloramphenicol acetyltransferase. The indicator or indicator gene may be functional or non-functional as described in PCT International Application No. PCT/US97/01609, filed Jan. 29, 1997.

The phenotypic drug susceptibility and resistance tests of this invention may be carried out in one or more host cells as described in PCT International Application No. PCT/US97/01609, filed Jan. 29, 1997 which is incorporated herein by reference. Viral drug susceptibility is determined as the concentration of the anti-viral agent at which a given percentage of indicator gene expression is inhibited (e.g. the IC50 for an anti-viral agent is the concentration at which 50% of indicator gene expression is inhibited). A standard curve for drug susceptibility of a given anti-viral drug can be developed for a viral segment that is either a standard laboratory viral segment or from a drug-naive patient (i.e. a patient who has not received any anti-viral drug) using the method described in the aforementioned patent application. Correspondingly, viral drug resistance is a decrease in viral drug susceptibility for a given patient measured either by comparing the drug susceptibility to such a given standard or by making one or more sequential measurements in the same patient over time, as determined by increased inhibition of indicator gene expression (i.e. decreased indicator gene expression).

The anti-viral drugs being added to the test system are added at selected times depending upon the target of the anti-viral drug. For example, in the case of HIV protease inhibitors, including saquinavir, ritonavir, indinavir, and nelfinavir, they are added to packaging host cells at the time of or shortly after their transfection with a resistance test vector, at an appropriate range of concentrations. HIV reverse transcriptase inhibitors, including AZT, ddI, ddC, d4T, 3TC, nevirapine and delavirdine, are added to target host cells at the time of or prior to infection by the resistance test vector viral particles, at an appropriate range of concentration. Alternatively, the anti-viral drugs may be present throughout the assay. The test concentration is selected from a range of concentrations which is typically between about 0.1 nM and about 100 $\mu$M and more specifically for each of the following drugs: AZT, from about 6 nM to about 400 $\mu$M; ddI, from about 15 nM to about 1,000 $\mu$M; 3TC, from about 9 nM to about 600 Ê$\mu$M; d4T, from about 6 nM to about 400 $\mu$M; ddC, from about 15 nM to about 1,000 $\mu$M; nevirapine, from about 0.7 nM to about 50 $\mu$M; delavirdine, from about 0.07 nM to about 5 $\mu$M; saquinavir, from about 0.02 nM to about 1.5 $\mu$M; indinavir, from about 0.02 nM to about 1.5 $\mu$M; nelfinavir, from about 0.02 nM to about 1.5 $\mu$M; and ritonavir, from about 0.05 nM to about 3 $\mu$M.

In another embodiment of this invention, a candidate NRTI antiretroviral compound is tested in the phenotypic drug susceptibility and resistance test using the resistance test vector comprising RT having mutations at codon 69 and 41 and 215. In another embodiment of this invention, a candidate NRTI antiretroviral compound is tested in the phenotypic drug susceptibility and resistance test using the resistance test vector comprising RT having mutations at one or more codons selected from the group consisting of 62, 75, 77, 116 and/or 151. In another embodiment of this invention, a candidate NRTI antiretroviral compound is tested in the phenotypic drug susceptibility and resistance test using the resistance test vector comprising RT having mutations at four or more codons selected from the group consisting M41L, D67N, K70R, L210W, T215Y/F and K219Q. In another embodiment of this invention, a candidate NRTI antiretroviral compound is tested in the phenotypic drug susceptibility and resistance test using the resistance test vector comprising RT having mutations at codon 69 (either T69SSA, T69SSG, T69SSS) and M41L and T215Y and mutation at one or more codons selected from the group consisting of M184V/I, L74V, A62V, V75M. The candidate anti-viral compound is added to the test system at an appropriate range of concentrations and at the transfection step. Alternatively, more than one candidate anti-viral compound may be tested or a candidate anti-viral compound may be tested in combination with an approved anti-viral drug such as AZT, ddI, ddC, d4T, 3TC, delavirdine, nevirapine, saquinavir, ritonavir, indinavir, nelfinavir or a compound which is undergoing clinical trials such as abacavir, or amprenavir or efavirenz. The effectiveness of the candidate anti-viral will be evaluated by measuring the expression or inhibition of the indicator gene. In another aspect of this embodiment, the drug susceptibility and resistance test may be used to screen for viral mutants. Following the identification of resistant mutants to either known antiretrovirals or candidate antiretrovirals the resistant mutants are isolated and the DNA is analyzed. A library of viral resistant mutants can thus be assembled enabling the screening of candidate NRTI antiretrovirals, alone or in combination. This will enable one of ordinary skill to identify effective NRTI antiretrovirals and design effective therapeutic regimens.

General Materials And Methods

Most of the techniques used to construct vectors, and transfect and infect cells, are widely practiced in the art, and most practitioners are familiar with the standard resource materials which describe specific conditions and procedures. However, for convenience, the following paragraphs may serve as a guideline.

"Plasmids" and "vectors" are designated by a lower case p followed by letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

Construction of the vectors of the invention employs standard ligation and restriction techniques which are well understood in the art (see Ausubel et al., (1987) Current Protocols in Molecular Biology, Wiley—Interscience or Maniatis et al., (1992) in Molecular Cloning: A laboratory Manual, Cold Spring Harbor Laboratory, N.Y.). Isolated plasmids, DNA sequences, or synthesized oligonucleotides are cleaved, tailored, and relegated in the form desired. The sequences of all DNA constructs incorporating synthetic DNA were confirmed by DNA sequence analysis (Sanger et al. (1977) Proc. Natl. Acad. Sci. 74, 5463–5467).

"Digestion" of DNA refers to catalytic cleavage of the DNA with a restriction enzyme that acts only at certain sequences, restriction sites, in the DNA. The various restriction enzymes used herein are commercially available and their reaction conditions, cofactors and other requirements are known to the ordinarily skilled artisan. For analytical purposes, typically 1 µg of plasmid or DNA fragment is used with about 2 units of enzyme in about 20 µl of buffer solution. Alternatively, an excess of restriction enzyme as used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods of Enzymology 65:499–560 (1980).

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 200 C. in 50 mM Tris (pH7.6) 50 mM NaCl, 6 mM $MgCl_2$, 6 mM DTT and 5–10 dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 15–50 µl volumes under the following standard conditions and temperatures: 20 mM Tris-Cl pH 7.5, 10 mM $MgCl_2$, 10 mM DTT, 33 mg/ml BSA, 10 mM–50 mM NaCl, and either 40 µM ATP, 0.01–0.02 (Weiss) units T4 DNA ligase at 00 C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 mM total end concentration). Intermolecular blunt end ligations (usually employing a 10–30 fold molar excess of linkers) are performed at 1 µM total ends concentration.

"Transient expression" refers to unamplified expression within about one day to two weeks of transfection. The optimal time for transient expression of a particular desired heterologous protein may vary depending on several factors including, for example, any transacting factors which may be employed, translational control mechanisms and the host cell. Transient expression occurs when the particular plasmid that has been transfected functions, i.e., is transcribed and translated. During this time the plasmid DNA which has entered the cell is transferred to the nucleus. The DNA is in a nonintegrated state, free within the nucleus. Transcription of the plasmid taken up by the cell occurs during this period. Following transfection the plasmid DNA may become degraded or diluted by cell division. Random integration within the cell chromatin occurs.

In general, vectors containing promoters and control sequences which are derived from species compatible with the host cell are used with the particular host cell. Promoters suitable for use with prokaryotic hosts illustratively include the beta-lactamase and lactose promoter systems, alkaline phosphatase, the tryptophan (trp) promoter system and hybrid promoters such as tac promoter. However, other functional bacterial promoters are suitable. In addition to prokaryotes, eukaryotic microbes such as yeast cultures may also be used. Saccharomyces cerevisiae, or common baker's yeast is the most commonly used eukaryotic microorganism, although a number of other strains are commonly available. Promoters controlling transcription from vectors in mammalian host cells may be obtained from various sources, for example, the genomes of viruses such as: polyoma, simian virus 40 (SV40), adenovirus, retroviruses, hepatitis B virus and preferably cytomegaldvirus, or from heterologous mammalian promoters, e.g. β-actin promoter. The early and late promoters of the SV 40 virus are conveniently obtained as an SV40 restriction fragment which also contains the SV40 viral origin of replication. The immediate early promoter of the human cytomegalovirus is conveniently obtained as a HindIII restriction fragment. Of course, promoters from the host cell or related species also are useful herein.

The vectors used herein may contain a selection gene, also termed a selectable marker. A selection gene encodes a protein, necessary for the survival or growth of a host cell transformed with the vector. Examples of suitable selectable markers for mammalian cells include the dihydrofolate reductase gene (DHFR), the ornithine decarboxylase gene, the multi-drug resistance gene (mdr), the adenosine deaminase gene, and the glutamine synthase gene. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. The second category is referred to as dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern and Berg (1982) J. Molec. Appl. Genet. 1, 327), mycophenolic acid (Mulligan and Berg (1980) Science 209, 1422), or hygromycin (Sugden et al. (1985) Mol. Cell. Biol. 5, 410–413). The three examples given above employ bacterial genes under eukaryotic control to convey resistance to the appropriate drug neomycin (G418 or genticin), xgpt (mycophenolic acid) or hygromycin, respectively.

"Transfection" means introducing DNA into a host cell so that the DNA is expressed, whether functionally expressed or otherwise; the DNA may also replicate either as an extrachromosomal element or by chromosomal integration. Unless otherwise provided, the method used herein for transformation of the host cells is the calcium phosphate co-precipitation method of Graham and van der Eb (1973) Virology 52, 456–457. Alternative methods for transfection are electroporation, the DEAE-dextran method, lipofection and biolistics (Kriegler (1990) Gene Transfer and Expression: A Laboratory Manual, Stockton Press).

Host cells may be transfected with the expression vectors of the present invention and cultured in conventional nutrient media modified as is appropriate for inducing promoters, selecting transformants or amplifying genes. Host cells are cultured in F12:DMEM (Gibco) 50:50 with added glutamine and without antibiotics. The culture conditions, such as temperature, pH and the like, are those previously used with the host cell selected for expression, and will be apparent to the ordinarily skilled artisan.

The following examples merely illustrate the best mode now known for practicing the invention, but should not be construed to limit the invention. All publications and patent applications cited in this specification are herein incorporated by reference in their entirety as if each individual publication or patent application were specifically and individually indicated to be incorporated by reference.

EXAMPLE 1

Phenotypic Drug Susceptibility And Resistance Test Using Resistance Test Vectors Phenotypic drug susceptibility and resistance tests are carried out using the means and methods described in PCT International Application No. PCT/US97/01609, filed Jan. 29, 1997 which is hereby incorporated by reference.

In these experiments patient-derived segment(s) corresponding to the HIV protease and reverse transcriptase coding regions were either patient-derived segments amplified by the reverse transcription-polymerase chain reaction method (RT-PCR) using viral RNA isolated from viral particles present in the serum of HIV-infected individuals or were mutants of wild type HIV-1 made by site directed mutagenesis of a parental clone of resistance test vector DNA. Isolation of viral RNA was performed using standard procedures (e.g. RNAgents Total RNA Isolation System, Promega, Madison Wis. or RNAzol, Tel-Test, Friendswood, Tex.). The RT-PCR protocol was divided into two steps. A retroviral reverse transcriptase [e.g. Moloney MuLV reverse transcriptase (Roche Molecular Systems, Inc., Branchburg, N.J.), or avian myeloblastosis virus (AMV) reverse transcriptase, (Boehringer Mannheim, Indianapolis, Ind.)] was used to copy viral RNA into cDNA. The cDNA was then amplified using a thermostable DNA polymerase [e.g. Taq (Roche Molecular Systems, Inc., Branchburg, N.J.), Tth (Roche Molecular Systems, Inc., Branchburg, N.J.), PrimeZyme (isolated from Thermus brockianus, Biometra, Gottingen, Germany)] or a combination of thermostable polymerases as described for the performance of "long PCR" (Barnes, W. M., (1994) Proc. Natl. Acad. Sci, USA 91, 2216–2220) [e.g. Expand High Fidelity PCR System (Taq+ Pwo), (Boehringer Mannheim. Indianapolis, Ind.) OR Gene-Amp XL PCR kit (Tth+Vent), (Roche Molecular Systems, Inc., Branchburg, N.J.)].

The primers, ApaI primer (PDSApa) and Age! primer (PDSAge) used to amplify the "test" patient-derived segments contained sequences resulting in ApaI and AgeI recognition sites being introduced into the 5' and 3' termini of the PCR product, respectively as described in PCT International Application No. PCT/US97/01609, filed Jan. 29, 1997.

Resistance test vectors incorporating the "test" patient-derived segments were constructed as described in PCT International Application No. PCT/US97/01609, filed Jan. 29, 1997 using an amplified DNA product of 1.5 kB prepared by RT-PCR using viral RNA as a template and oligonucleotides PDSApa (1) and PDSAge (2) as primers, followed by digestion with ApaI and AgeI or the isoschizimer PINAI. To ensure that the plasmid DNA corresponding to the resultant resistance test vector comprises a representative sample of the HIV viral quasi-species present in the serum of a given patient, many (>100) independent $E.$ $coli$ transformants obtained in the construction of a given resistance test vector were pooled and used for the preparation of plasmid DNA.

A packaging expression vector encoding an amphotrophic MuLV 4070A env gene product enables production in a resistance test vector host cell of resistance test vector viral particles which can efficiently infect human target cells. Resistance test vectors encoding all HIV genes with the exception of env were used to transfect a packaging host cell (once transfected the host cell is referred to as a resistance test vector host cell). The packaging expression vector which encodes the amphotrophic MuLV 4070A env gene product is used with the resistance test vector to enable production in the resistance test vector host cell of infectious pseudotyped resistance test vector viral particles.

Resistance tests performed with resistance test vectors were carried out using packaging host and target host cells consisting of the human embryonic kidney cell line 293 (Cell Culture Facility, UC San Francisco, SF, Calif.) or the Jurkat leukemic T-cell line (Arthur Weiss, UC San Francisco, SF, Calif.).

Resistance tests were carried out with resistance test vectors using two host cell types. Resistance test vector viral particles were produced by a first host cell (the resistance test vector host cell) that was prepared by transfecting a packaging host cell with the resistance test vector and the packaging expression vector. The resistance test vector viral particles were then used to infect a second host cell (the target host cell) in which the expression of the indicator gene is measured.

The resistance test vectors containing a functional luciferase gene cassette were constructed and host cells were transfected with the resistance test vector DNA. The resistant test vectors contained patient-derived reverse transcriptase and protease sequences that were either susceptible or resistant to the antiretroviral agents, such as nucleoside reverse transcriptase inhibitors, non-nucleoside reverse transcriptase inhibitors and protease inhibitors. The resistance test vector viral particles produced by transfecting the resistance test vector DNA into host cells, either in the presence or absence of protease inhibitors, were used to infect target host cells grown either in the absence of NRTI or NNRTI or In the presence of increasing concentrations of the drug. The amount of luciferase activIty produced in infected target host cells in the presence of drug was compared to the amount of luciferase produced in infected target host cells in the absence of drug. Drug resistance was measured as the amount of drug required to inhibit by 50% the luciferase activity detected in the absence of drug (Inhibitory concentration 50%, IC50). The IC50 values were determined by plotting percent drug inhibition vs. log 10 drug concentration.

Figure 3:
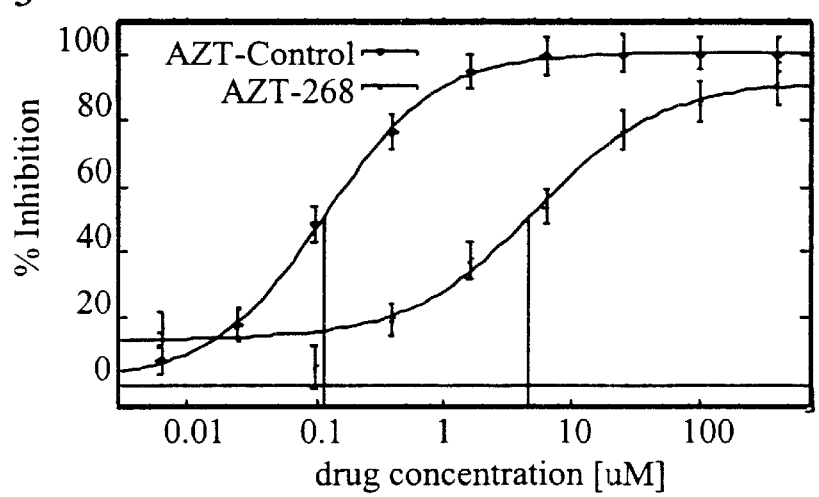
Figure 3:
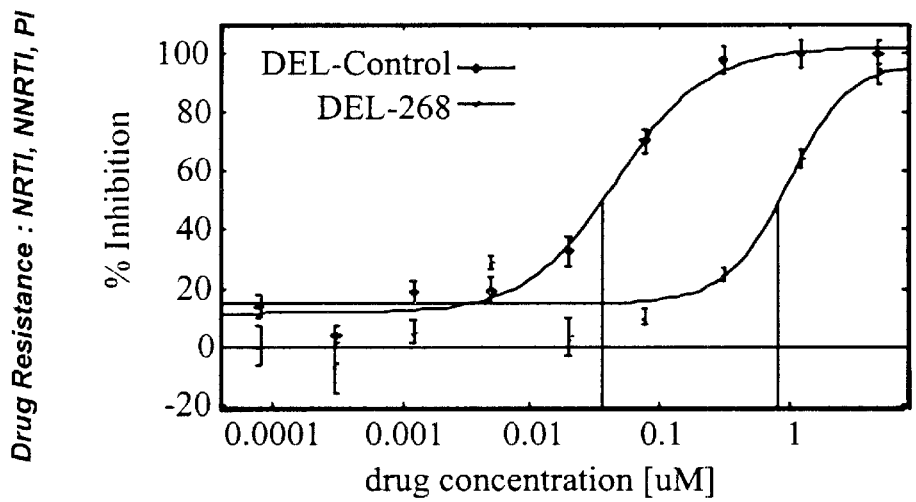
Figure 3:
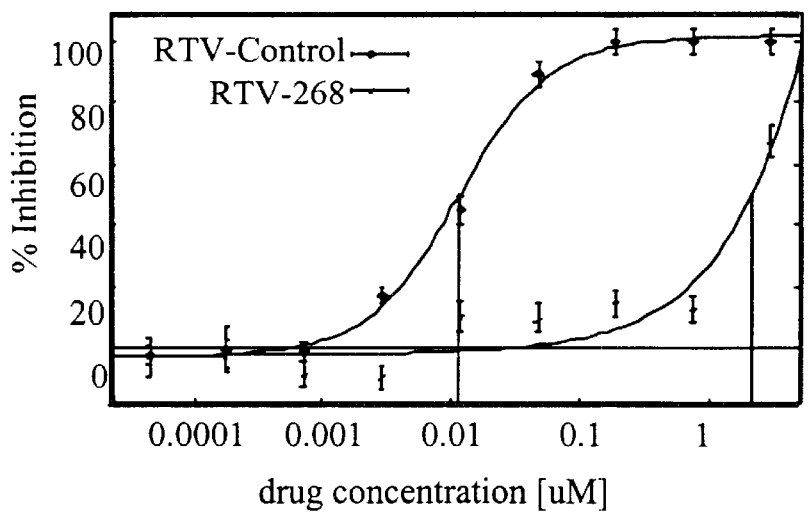
Figure 4:
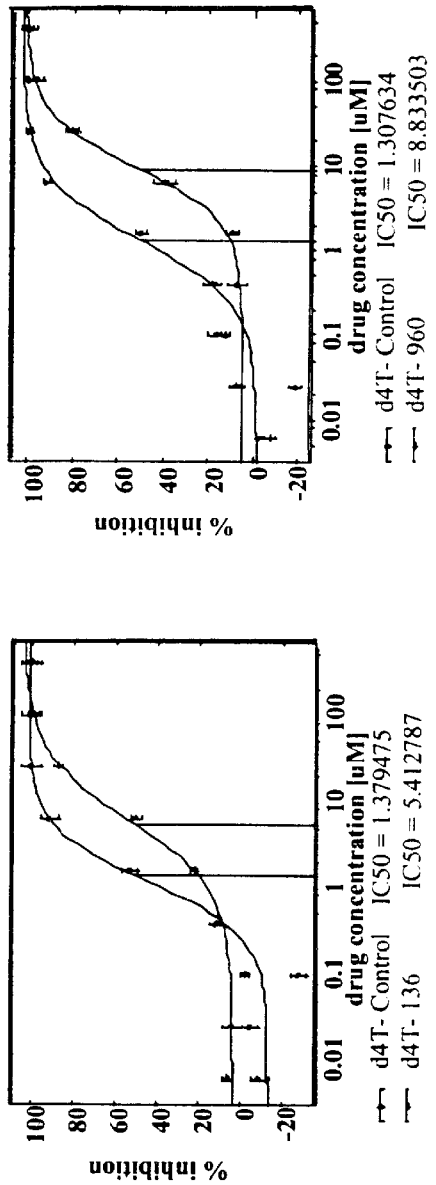
Figure 4:
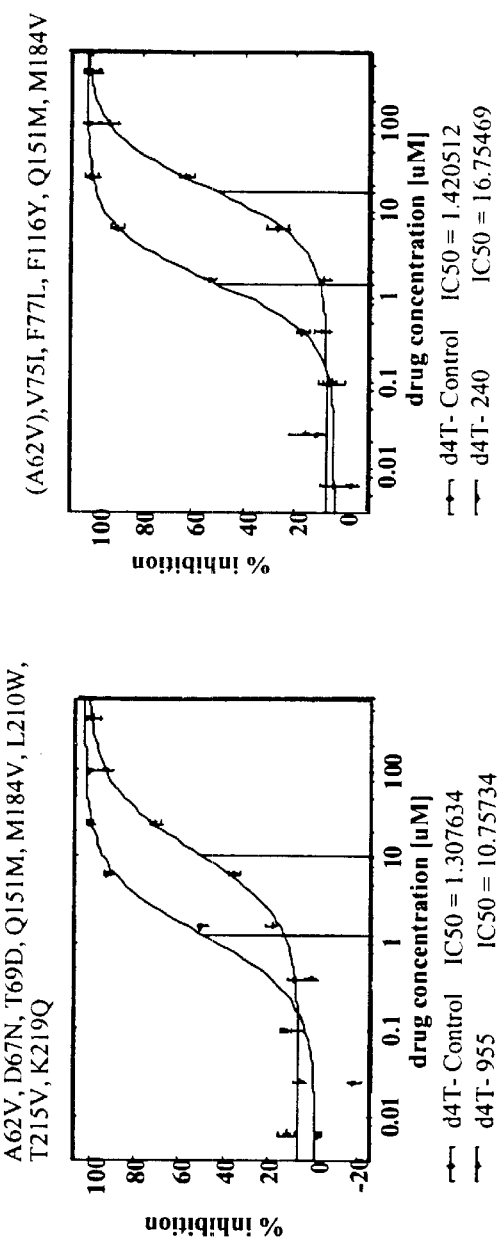

Host cells were seeded in 10-cm-diameter dishes and were transfected several days after plating with resistance test vector plasmid DNA and the envelope expression vector. Transfections were performed using a calcium-phosphate precipitation procedure. The cell culture media containing the DNA precipitate was replaced with fresh medium, from one to 24 hours, after transfection. Cell culture media containing resistance test vector viral particles was harvested one to four days after transfection and was passed through a 0.45-mm filter before being stored at −80° C. HIV capsid protein (p24) levels in the harvested cell culture media were determined by an EIA method as described by the manufacturer (SIAC; Frederick, Md.). Before infection, target cells (293 and 293/T) were plated in cell culture media. Control infections were performed using cell culture media from mock transfections (no DNA) or transfections containing the resistance test vector plasmid DNA without the envelope expression plasmid. One to three or more days after infectIon the media was removed and cell lysis buffer (Promega) was added to each well. Cell lysates were assayed for luciferase activity (FIG. 3). The inhibitory effect of the drug was determined using the following equation:

$$\% \text{ luciferase inhibition} = 1 - (RLUluc[\text{drug}] \div RLUluc) \times 100$$

where RLUluc [drug] is the relative light unit of luciferase activity in infected cells in the presence of drug and RLUluc is the Relative Light Unit of luciferase activity in infected cells in the absence of drug. IC50 values were obtained from the sigmoidal curves that were generated from the data by plotting the percent inhibition of luciferase activity vs. the log 10 drug concentration. The drug inhibition curves are shown in (FIG. 3).

EXAMPLE 2

Correlating Phenotypic Susceptibility and Genotypic Analysis

Phenotypic Susceptibility Analysis of Patient HIV Samples

Resistance test vectors are constructed as described in example 1. Resistance test vectors, or clones derived from the resistance test vector pools, are tested in a phenotypic assay to determine accurately and quantitatively the level of susceptibility to a panel of anti-retroviral drugs. This panel of anti-retroviral drugs may comprise members of the classes known as nucleoside-analog reverse transcriptase inhibitors (NRTIS), non-nucleoside reverse transcriptase inhibitors (NNRTIS), and protease inhibitors (PRIs). The panel of drugs can be expanded as new drugs or new drug targets become available. An IC50 is determined for each resistance test vector pool for each drug tested. The pattern of susceptibility to all of the drugs tested is examined and compared to known patterns of susceptibility. A patient sample can be further examined for genotypic changes correlated with the pattern of susceptibility observed.

Genotypic Analysis of Patient HIV Samples

Resistance test vector DNAs, either pools or clones, are analyzed by any of the genotyping methods described in Example 2. In one embodiment of the invention, patient HIV sample sequences are determined using viral RNA purification, RT/PCR and ABI chain terminator automated sequencing. The sequence that is determined is compared to control sequences present in the database or is compared to a sample from the patient prior to initiation of therapy, if available. The genotype is examined for sequences that are different from the control or pre-treatment sequence and correlated to the observed phenotype.

Phenotypic Susceptibility Analysis of Site Directed Mutants

Genotypic changes that are observed to correlate with changes in phenotypic patterns of drug susceptibility are evaluated by construction of resistance test vectors containing the specific mutation on a defined, wild-type (drug susceptible) genetic background. Mutations may be incorporated alone and/or in combination with other known drug resistance mutations that are thought to modulate the susceptibility of HIV to a certain drug or class of drugs. Mutations are introduced into the resistance test vector through any of the widely known methods for site-directed mutagenesis. In one embodiment of this invention the megaprimer PCR method for site-directed mutagenesis is used. A resistance test vector containing the specific mutation or group of mutations is then tested using the phenotypic susceptibility assay described above and the susceptibility profile is compared to that of a genetically defined wild-type (drug susceptible) resistance test vector which lacks the specific mutations. Observed changes in the pattern of phenotypic susceptibility to the antiretroviral drugs tested are attributed to the specific mutations introduced into the resistance test vector.

EXAMPLE 3

Correlating Phenotypic Susceptibility and Genotypic Analysis: D4T-Resistance Associated with Multi-Drug Resistance (MDR) Mutations Phenotypic Analysis of Resistance Test Vectors from Patients 96–136, 97–240, 98–955 and 98–960

Resistance test vectors were constructed as described in example 1 from a patient samples designated as 96–136, 97–240, 98–955 and 98–960. Patients 136 and 240 had been previously treated with regimens including d4T for various periods of time. The history of drug exposure for patients 955 and 960 is unknown. Isolation of viral RNA and RT/PCR was used to generate patient derived segments that comprised viral sequences coding for all of PR and aa 1–313 of RT. The patient derived segments were inserted into a indicator gene viral vector to generate resistance test vectors designated RTV-136, RTV-240, RTV-955 and RTV-960. The RTVs were tested using a phenotypic susceptibility assay to determine accurately and quantitatively the level of susceptibility to a panel of anti-retroviral drugs. This panel of anti-retroviral drugs comprised members of the classes known as NRTIs (AZT, 3TC, d4T, ddI, ddC, and abacavir), NNRTIs (delavirdine and nevirapine), and PRIs (indinavir, nelfinavir, ritonavir, and saquinavir). An IC50 was determined for each drug tested. Susceptibility of the patient virus to each drug was examined and compared to known patterns of susceptibility. A decrease in susceptibility to d4T compared to a wild-type control RTV was observed in each of these RTV pools. The patient samples were examined further for genotypic changes that could be associated with the observed pattern of d4T susceptibility.

Determination of Genotype of Patient RTV DNAs

RTV DNAs were analyzed by ABI chain terminator automated sequencing. The nucleotide sequence was compared to the consensus sequence of a wild type clade B HIV-1 (HIV Sequence Database Los Alamos, N. Mex.). The nucleotide sequence was examined for sequences that are different from the control sequence. RTV-136 contained mutations at M41L, D67N, V75I, F116Y, Q151 M, M184V, T200A, and T215Y. All mutations in RTV-136 were present as a mixture of wild-type and mutant amino acids at each position. RTV-240 contained mutations at A62V, S68G, V75I, F77L, F116Y, E138A, Q151M, and M184V. RTV-955 contained mutations at E6D, K20R, V35I, A62V, D67N, T69D, V75I, F77L, K101E, K103N, Y115F, F116Y, Q151M, I167V, Y181C, M184V, G190A, I202V, R211K, F214L, T215V, and K219Q. The mutations at positions 101, 103, 181 and 190 were present as a mixture of wild-type and mutant amino acids at each position. RTV-960 contained mutations at A33I, T39A, M41L, E44D, D67N, T69D, K103N, Q151M, M184I, G190A, L210W, R211K, T215Y, D218E, T240K, and A288S. The mutations at A62V, V75I, F77L, F116Y, and Q151M have been previously described to result in broad spectrum cross resistance to NRTIs and are known as multi-drug resistance (MDR) mutations. All of these RTV DNAs contained one or several of these MDR mutations. In addition some of the RTV DNAs had mutations associated with AZT-resistance (M41L, D67N, L210W, T215Y, and K219Q), ddC-resistance (T69D), NNRTI-resistance (K101E, K103N, Y181C, and G190A), 3TC-resistance (M184V), or previously uncharacterized mutations (E6D, K20R, A33I, T39A, E44D, S68G, Y115F, I167V, E138A, G196A, I202V, T215V, D218E, and T240K). The mutations at V35I, R211K, and F214L are known polymorphisms of the wild-type (drug-sensitive) variants of HIV.

Site Directed Mutagenesis

Resistance test vectors were constructed containing the Q151M mutation alone and in combination the V75I drug resistance mutations known to modulate the HIV susceptibility to NRTIs. Mutations were introduced into the resistance test vector using the mega-primer PCR method for site-directed mutagenesis. (Sakar G and Sommar S S (1994) *Biotechniques* 8(4), 404–407). A resistance test vector containing the Q151M mutation (Q151M-RTV) was tested using the phenotypic susceptibility assay described above and the results were compared to that of a genetically defined resistance test vector that was wild type at position 115. The pattern of phenotypic susceptibility to the NRTI, d4T in the Q151M-RTV was altered as compared to wild type. In the context of an otherwise wild type background (i.e. Q151M mutation alone) the Q151M-RTV was less susceptible to d4T than the wild type control RTV. Significant changes in susceptibility to AZT, ddC and ddI were also observed in the Q151M-RTV. The Q151M mutation was also introduced into a RTV containing a mutation at V75I. The addition of the V75I mutation onto the Q151M background resulted in an increased susceptibility to AZT and a decreased susceptibility to d4T. The V75I mutation alone had no effect on d4t-susceptibility and resulted in an increase in the susceptibility to AZT. RTVs were also constructed that contained mutations at A62V alone and in combination with V75I. These RTVs showed no differences in their susceptibility to d4T, compared to a wild-type RTV, however both showed slight increases in susceptibility to AZT.

EXAMPLE 4

Correlating Phenotypic Susceptibility and Genotypic Analysis: D4T-Resistance Associated with Insertions at Amino Acid 69 in Reverse Transcriptase Phenotypic Analysis of Resistance Test Vectors from Patients 97–621, 97–285, 98–690, 98–770 and 98–771

Resistance test vectors were constructed as described in example 1 from patient samples designated 97–621, 97–285, 98–690, 98–770 and 98–771. Patient samples 285 and 690 are serial samples obtained from the same patient at 6 month intervals. Patients 285/690, 770 and 771 had been previously treated with regimens including d4T for various periods of time. The history of drug exposure for patient 621 is unknown.

Patient Histories on Virus Samples with 69SSX Insertions

Patient VL#770 (JCW) was initially treated with AZT monotherapy. ddC was then added to the regimen, and the two drugs were given for a period of approximately 8 months. For a period of 15 months, the treatment was unknown and then patient VL#770 (JCW) was treated for approximately 2½ years with a combination of AZT and 3TC. Patient VL#285/690 (JWA) was treated with AZT monotherapy for approximately 1 year and 9 months before being switched to ddI monotherapy for a period of 8 months. He returned to AZT monotherapy for 1 year 3 months and then was treated with ddC for almost 2 years. The treatment was changed to a combination of AZT and 3TC for almost a year and then was changed to a combination of d4T/3TC/NFV for a period of approximately 9 months. Patient VL#771 (BMM) was initially treated with a combination of AZT, ddC and the PRI, RTV. 3TC was then added to this combination until treatment was switched to d4T and RTV. This treatment continued for approximately 6 months and was then changed to a combination of 3TC/d4T/ddI and RTV. There was a period of approximately 6 months in which no treatment was received. This was followed by treatment with AZT, 3TC and ddI. The combination was then switched to 3TC, d4T and IDV. Patient VL#1057 (DHW) was treated with AZT monotherapy for approximately 3 years before being switched to ddI monotherapy for 1 year. There was a period of approximately 8 months in which no treatment was received. This was followed by treatment with AZT and 3TC for 1 year. The treatment with AZT continues but 3TC was replaced by d4T and the PRI, IDV was added. The d4T was then switched back to 3TC for a short period until it was replaced by the NNRTI, DEL. Isolation of viral RNA and RT/PCR was used to generate patient derived segments that comprised viral sequences coding for all of PR and aa 1–313 of RT. The patient derived segments were inserted into an indicator gene viral vector to generate resistance test vectors designated RTV-621, RTV-285, RTV-690, RTV-770 and RTV-771. The RTVs were tested using a phenotypic susceptibility assay to determine accurately and quantitatively the level of susceptibility to a panel of anti-retroviral drugs. This panel of anti-retroviral drugs comprised members of the classes known as NRTIs (AZT, 3TC, d4T, ddI, ddC, and abacavir), NNRTIs (delavirdine and nevirapine), and PRIs (indinavir, nelfinavir, ritonavir, and saquinavir). An IC50 was determined for each drug tested. Susceptibility of the patient virus to each drug was examined and compared to known patterns of susceptibility. A decrease in susceptibility to d4T compared to a wild-type control RTV was observed in each of these RTV pools. The patient samples were examined further for genotypic changes that could be associated with the observed pattern of d4T susceptibility.

Determination of Genotype of Patient RTV DNAs

RTV DNAs were analyzed by ABI chain terminator automated sequencing. The nucleotide sequence was compared to the consensus sequence of a wild type clade B HIV-1 (HIV Sequence Database Los Alamos, N. Mex.). The nucleotide sequence was examined for sequences that are different from the control sequence. RTV-621 contained mutations at M41L, A62V, T69SSS, V75M, M184V, L210W, and T215Y. Mutations in RTV-621 at positions 41, 62, and 75 were present as a mixture of wild-type and mutant amino acids at each position. RTV-285 contained mutations at M41L, A62V, T69SSA, L74V, A158S, I178M, M184V, T200A, L210W, and T215Y. RTV-690 contained mutations at K20R, M41L, A62V, T69SSA, L74V, A158S, I178M, Y181C, G190A,L210W, and T215Y. The mutations at positions 158 and 181 were present as a mixture of wild-type and mutant amino acids at each position. RTV-770 contained mutations at V21I, M41L, T69SSG, V75M, K102M, K103R, V179I, M184V, T215Y, V241L, L283I, and E297R. The mutations at positions 69 and 75 were present as a mixture of wild-type and mutant amino acids at each position. RTV-771 contained mutations at E6D, V35I, M41L, T69SSS, V75M, I135V, Q174R, D177E, M184V, T200I, L210W, R211K, T215Y, R284K, A288S, and E291D. The mutations at positions 174 and 200 were present as a mixture of wild-type and mutant amino acids at each position. All of these RTV DNAs had an unusual insertion of extra amino acids at or around position 69 In reverse transcriptase. The insertion is described here as T69SSX, where X indicates either a glycine (G), a serine (S), or an alanine (A) The mutation at A62V has been previously described as a member of the multi-drug resistance (MDR) mutations to contribute to broad spectrum cross resistance to NRTIs as described in example 3. In addition all of the RTV DNAs had some subset of the mutations associated with AZT-resistance (M41L, D67N, L210W, T215Y, and K219Q), ddC-resistance (L74V, L74I, T69D), NNRTI-resistance (K103N, Y181C, and G190A), 3TC-resistance (M184V), or previously uncharacterized mutations (V75M, A158S, K20R, V21I, K102M, V179I, V241L, I283I, E297R, E6D, Q174R, D177E, R284K, A288S, E291D). The mutations at V35I, K103R, I135V, D177E, I178M, V179I, T200A/I, R211K, and F214L are previously observed polymorphisms of the wild-type (drug-sensitive) variants of HIV.

Reverse Mutagenesis

The role of the T69SSX mutation in d4T resistance was further examined by the procedure commonly known as reverse mutagenesis. A functional clone was isolated from the RTV-285 pool that contained the following mutations (M41L, A62V, T69SSA, L74V, A158S, I178M, M184V, T200A, L210W, and T215Y) in RT. Site directed mutagenesis was used to specifically change the triplet "SSA" to a single threonine (T) at position 69. This revertant, 285-1 (SSA69T), contained all of the mutations present in the 285-1 clone except for the SSA insertion at position 69. The 285-1 (SSA69T) revertant showed a significant increase in susceptibility to both d4T (3 fold) and AZT (30 fold). Further evidence for the role of the T69SSX insertion in NRTI resistance came from the examination of individual clones isolated from the RTV-770 pool. Two classes of clones were present in the RTV-770 pool: the first class contained mutations at V21I, M41L, K102M, K103R, V179I, M184V, T215Y, V241L, L283I, and E297R, the second class contained all of the mutations present in the first class and in addition had mutations at T69SSG and V75M. The second class of mutations, those with mutations at 69 and 75, showed significant increases in susceptbility to both d4T (4 fold) and AZT (30 fold).

Site Directed Mutagenesis

Resistance test vectors were constructed containing the T69SSA mutation alone and in combination with other drug resistance mutations known or suspected to modulate the HIV susceptibility to NRTIs. Mutations were introduced into the resistance test vector using the mega-primer PCR method for site-directed mutagenesis. (Sakar G and Sommar S S (1994) Biotechniques 8(4), 404–407). A resistance test vector containing the T69SSA mutation (T69SSA-RTV) was tested using the phenotypic susceptibility assay described above and the results were comoared to that of a genetically defined resistance test vector that was wild type (T) at position 69. The T69SSA-RTV showed a 2-fold decrease in susceptibility to d4T compared to a wild type RTV. A small but significant change in susceptibility to AZT was also observed in the T69SSA-RTV.

The T69SSA mutation was also introduced into a RTV containing a mutation at V75I. The addition of the V75I mutation onto the T69SSA background resulted in an increased susceptibility to AZT and a decreased susceptibility to d4T. The V75I mutation alone had no effect on d4t-susceptibility and resulted in an increase in the susceptibility to AZT.

The T69SSA mutation was also introduced into a RTV containing a mutation at A62V. The A62V mutation alone had no effect on the susceptibility to any of the RT inhibitors tested. The addition of the A62V mutation onto the T69SSA background had no effect on the susceptibility to d4T but resulted in a significant decrease in susceptibility to AZT (6 fold).

A RTV was constructed containing mutations at A62V, T69SSA, and V75I. The triple mutant showed only a very small decerase in susceptibility to AZT (2 fold) (the same as T69SSA alone) and a small (less than 2 fold) increase in susceptibility to AZT.

RTVs were constructed that contained T69SSA insertion in conjunction with the AZT-resistance mutations M41L, A62V, T215Y and the 3tc-resistance mutation M184V in various combinations. The RTV containing mutaions at M41L, T169SSA and T215Y showed a significant decrease in susceptibility to both d4T (5 fold) and AZT (160 fold). The addition of an A62V mutation onto this background further decreased the susceptibility to both d4T (10 fold) and AZT (>1000 fold). The presence of the M184V mutation had no effect on the susceptibility to d4T but causes an increase in the susceptibility to AZT.

A resistance test vector was constructed containing mutations at M41L, T69SSA, T215Y and L210W. The introduction of the L210W mutation into an RTV containing the three mutations (M41L, T69SSA, and T215Y) resulted in a substantial decrease in susceptibility to AZT (greater than 1000-fold) compared to the 140-fold decrease in susceptibility observed for AZT in M41L-T69SSA-T215Y-RTV. The L210W mutation had little effect on the susceptibility to the other NRTIs when compared to M41L-T69SSA-T215Y-RTV. The decreased susceptibilities to ddC (3-fold), ddI (3.5-fold), 3TC (17-fold), d4T (10-fold), and abacavir (14-fold) observed for M41L-T69SSA-T215Y-L210W-RTV changed only slightly when compared to M41L-T69SSA-T215Y-RTV. The L210W mutation had no additional effect on susceptibility to the NNRTIs, DEL (0.13-fold) and NEV (0.42-fold), compared to M41L-T69SSA-T215Y-RTV, which also displayed a slight increase in susceptibility to DEL and NEV.

A RTV was constructed which contained four mutations: M41L, A62V, T69SSA, and T215Y. This vector, M41L-A62V-T69SSA-T215Y-RTV, displayed a substantial decrease in susceptibility to AZT (greater than 1000-fold), wild-type susceptibility to ddC (2.1-fold), a slight decrease in susceptibility to ddI (3-fold), a slight decrease in susceptibility to 3TC (8-fold), a slight decrease in susceptibility to d4T (8-fold), and a slight decrease in susceptibility to abacavir (10-fold). The vector displayed an increase in susceptibility to the NNRTIs, DEL (0.2-fold) and NEV (0.8-fold).

The L210W mutation was also introduced into the vector containing four other mutations: M41L, A62V, T69SSA, and T215Y. This vector, M41L- A62V-T69SSA-T215Y-L210W-RTV, displayed a substantial decrease in susceptibility to AZT (greater than 1000-fold), a slight decrease in susceptibility to ddC (2.1-fold), a slight decrease in susceptibility to ddI (3-fold), a moderate decrease in susceptibility to 3TC (22-fold), a moderate decrease in susceptibility to d4T (13-fold), and a moderate decrease in susceptibility to abacavir (16-fold). The vector displayed an increase in susceptibility to the NNRTIs, DEL (0.2-fold) and NEV (0.6-fold) The susceptibilitie s observed for M41L-A62V-T69SSA-T215Y-L210W-RTV were similar to those observed for the vector containing the M41L, A62V, T69SSA, and T215Y mutations but lacking the L210W mutation.

The T215Y mutation was introduced into a vector containing the A62V and T69SSA mutations. The introduction of the T215Y mutation resulted in a substantial decrease in susceptibility to AZT (1000-fold) compared to A62V-T69SSA-RTV, which displayed only a slight decrease in susceptibility to AZT (7-fold). The susceptibility to the other inhibitors was similar to the susceptibilities observed for the vector without the T215Y mutation. The A62V-T69SSA-T215Y-RTV displayed wild-type susceptibility to ddC (1.3- fold), a slight decrease in susceptibility to ddI (2.5-fold), a moderate decrease in susceptibility to 3TC (15-fold), a slight decrease in susceptibility to d4T (7-fold), and a slight decrease in susceptibility to abacavir (10-fold). The vector displayed increases in susceptibility to the both NNRTIs, DEL (0.3-fold) and NEV (0.6-fold).

The L74V mutation was also introduced into a vector containing the A62V and T69SSA mutations. The susceptibility to the inhibitors tested was similar to the susceptibilities observed for the vector without the L74V mutation and similar to the vector containing the T215Y mutation along with the A62V and T69SSA mutations. The greatest change was a shift of the susceptibility back to wild-type observed for AZT in A62V-T69SSA-L74V-RTV. The A62V-T69SSA-L74V-RTV displayed wild-type susceptibility to ddC (1.8-fold), wild-type susceptibility to ddI (1.9-fold), a slight decrease in susceptibility to 3TC (2.5-fold), wild-type susceptibility to d4T (1.5-fold), and a slight decrease in susceptibility to abacavir (3-fold). The vector displayed slight increases in susceptibility to the both NNRTIs, DEL (0.4-fold) and NEV (0.3-fold).

A RTV was constructed containing mutations at M41L, T69SSA, T215Y L210W and V75M. The introduction of the V75M mutation into an RTV containing the other four mutations (M41L, T69SSA, L210W and T215Y) had little effect on the susceptibilities compared to the vector without the V75M mutation. M41L-T69SSA-T215Y-L210W-V75M-RTV displayed a substantial decrease in susceptibility to AZT (greater than 1000-fold), a slight decrease in susceptibility to ddC (2.9-fold), a slight decrease in susceptibility to ddI (3.5-fold), a moderate decrease in susceptibility to 3TC (17-fold), a moderate decrease in susceptibility to d4T (11-fold), and a moderate decrease in susceptibility to abacavir (19-fold). The vector displayed an increase in susceptibility to the NNRTIs, DEL (0.25-fold) and NEV (0.5-fold).

EXAMPLE 5

Correlating Phenotypic Susceptibility and Genotypic Analysis: D4T-Resistance Associated with Complex Combinations of Multiple AZT-Resistance Mutaions Phenotypic Analysis of Resistance Test Vectors from Patients 98–757, 98–844, 98–937, 98–964 and 98–966

Resistance test vectors were constructed as described in example 1 from a patient samples designated 98–844, 98–937, 98–964 and 98–966. All of these patients had been previously treated with regimens including d4T for various periods of time. Isolation of viral RNA and RT/PCR was used to generate patient derived segments that comprised viral sequences coding for all of PR and aa 1–313 of RT. The patient derived segments were inserted into a indicator gene viral vector to generate resistance test vectors designated RTV-757, RTV-844. RTV-937, RTV-964 and RTV-966. The RTVs were tested using a phenotypic susceptibility assay to determine accurately and quantitatively the level of susceptibility to a panel of anti-retroviral drugs. This panel of anti-retroviral drugs comprised members of the classes known as NRTIs (AZT, 3TC, d4T, ddI, ddC, and abacavir), NNRTIs (delavirdine and nevirapine), and PRIs (indinavir, nelfinavir, ritonavir, and saquinavir). An IC50 was determined for each drug tested. Susceptibility of the patient virus to each drug was examined and compared to known patterns of susceptibility. A decrease in susceptibility to d4T compared to a wild-type control RTV was observed in each of these RTV pools. The patient samples were examined further for genotypic changes that could be associated with the observed pattern of d4T susceptibility.

Determination of Genotype of Patient RTV DNAs

RTV DNAs were analyzed by ABI chain terminator automated sequencing. The nucleotide sequence was compared to the consensus sequence of a wild type clade B HIV-1 (HIV Sequence Database Los Alamos, N. Mex.). The nucleotide sequence was examined for sequences that are different from the control sequence. RTV-757 contained mutations at V35I, D67N, T69D, K70R, V106A, V108I, L109V, Y181C, V189L, T200A, I202T, R211K, T215F, D218E, K219Q, H221Y, L228H, L283I, and R284K. Mutations at positions 106, 108 and 109 were present as a mixture of wild-type and mutant amino acids at each position. RTV-844 contained mutations at M41L, D67N, I135V, L210W, T215Y, and K219N. RTV-937 contained mutations at P1L, P9R, K20R, V35T, K64Y, D67N, K70R, V75M, G99R, I135V, K173E, Y188L, R211H, T215F, D218E, and K219Q. RTV-964 contained mutations at M41L, K43E, D67N, K70R, L74I, V75S, Y181I, R211T, T215Y, D218E, and K219Q. RTV-966 contained mutations at K20R, T39D, M41L, E44D, D67N, L74V, A98S, V118I, I135T, K166R, K173T, M184V, G196E, L210W, R211K, T215Y, D218E, K219R, L228H, V245E, K277R, T286A, A288T, V293I. All of these RTV DNAs contained one or several mutations previously associated with AZT-resistance (M41L, D67N, L210W, T215F/Y, and K219Q/R), ddC-resistance (T69D, L74I/V), NNRTI-resistance (V106A, V108I, Y181C/I, and Y188L), 3TC-resistance (M184V), or previously uncharacterized mutations (P1L, P9R, K20R, T39D, K43E, E44D, K64Y, V75M/S, G99R, L109V, V118I, K173E/T, I202T, R211H/T, D218E, K219N, H221Y, L228H, L283I, R284K, and A288T). The mutations at (V35I/T, A98S, I135V/T, K166R, G196E, T200A, R211K, F214L, V245E, K277R, T286A, and V293I are known polymorphisms of the wild-type (drug-sensitive) variants of HIV.

The mutations responsible for the decreased susceptibility to d4T in these patient samples are not obvious. There are patient samples that contain many of the same mutations found in these patients that do not show decreased susceptibility to d4T.

Site Directed Mutagenesis

Resistance test vectors containing five (M41L, D67N, K70R, T215Y, K219Q) or six (M41L, D67N, K70R, L210W, T215Y, K219Q) AZT-resistance associated mutations were constructed by site directed mutagenesis. Phenotypic susceptibility to NRTIs were determined. Significant decreases in susceptiblity to AZT (75–180 fold) and d4T (2 fold) were observed in these RTVs.

EXAMPLE 6

Predicting Response to Nucleoside Reverse Transcriptase Inhibitors by Characterization of Amino Acid Changes in HIV-1 Reverse Transcriptase Phenotypic and Genotypic Correlation of Mutations at Amino Acid 69 of HIV-1 Reverse Transcriptase In one embodiment of this invention, changes in the amino acid at position 69 of the reverse transcriptase protein of HIV-1 is evaluated using the following method comprising: (i) collecting a biological sample from an HIV-1 infected subject; (ii) evaluating whether the biological sample contains nucleic acid encoding HIV-1 reverse transcriptase having a mutation at codon 69. A reduction in d4T susceptibility and decreased AZT susceptibility is correlated with the presence of a mutation at codon 69 (T69SSX) either alone or on a background of other NRTI-resistance mutations (for example M41L, A62V, D67N, K70R, L74V, V75I/M, T215Y/F, K219Q).

The biological sample comprises whole blood, blood components including peripheral mononuclear cells (PBMC), serum, plasma (prepared using various anticoagulants such as EDTA, acid citrate-dextrose, heparin), tissue biopsies, cerebral spinal fluid (CSF), or other cell, tissue or body fluids. In another embodiment, the HIV-1 nucleic acid (genomic RNA) or reverse transcriptase protein can be isolated directly from the biological sample or after purification of virus particles from the biological sample. Evaluating whether the amino acid at position 69 of the HIV-1 reverse transcriptase is mutated, can be performed using various methods, such as direct characterization of the viral nucleic acid encoding reverse transcriptase or direct characterization of the reverse transcriptase protein itself. Defining the amino acid at position 69 of reverse transcriptase can be performed by direct characterization of the reverse transcriptase protein by conventional or novel amino acid sequencing methodologies, epitope recognition by antibodies or other specific binding proteins or compounds. Alternatively, the amino acid at position 69 of the HIV-1 reverse transcriptase protein can be defined by characterizing amplified copies of HIV-1 nucleic acid encoding the reverse transcriptase protein. Amplification of the HIV-1 nucleic acid can be performed using a variety of methodologies including reverse transcription-polymerase chain reaction (RT-PCR), NASBA, SDA, RCR, or 3SR as would be known to the ordinarily skilled artisan. Evaluating whether the nucleic acid encoding HIV reverse transcriptase has a mutation at codon 69 can be performed by direct nucleic acid sequencing using various primer extension-chain termination (Sanger, ABI/PE and Visible Genetics) or chain cleavage (Maxam and Gilbert) methodologies or more recently developed sequencing methods such as matrix assisted laser desorption-ionization time of flight (MALDI-TOF) or mass spectrometry (Sequenom, Gene Trace Systems). Alternatively, the nucleic acid sequence encoding amino acid position 69 can be evaluated using a variety of probe hybridization methodologies, such as genechip hybridization sequencing (Affymetrix), line probe assay (LiPA; Murex), and differential hybridization (Chiron).

Figure 5:
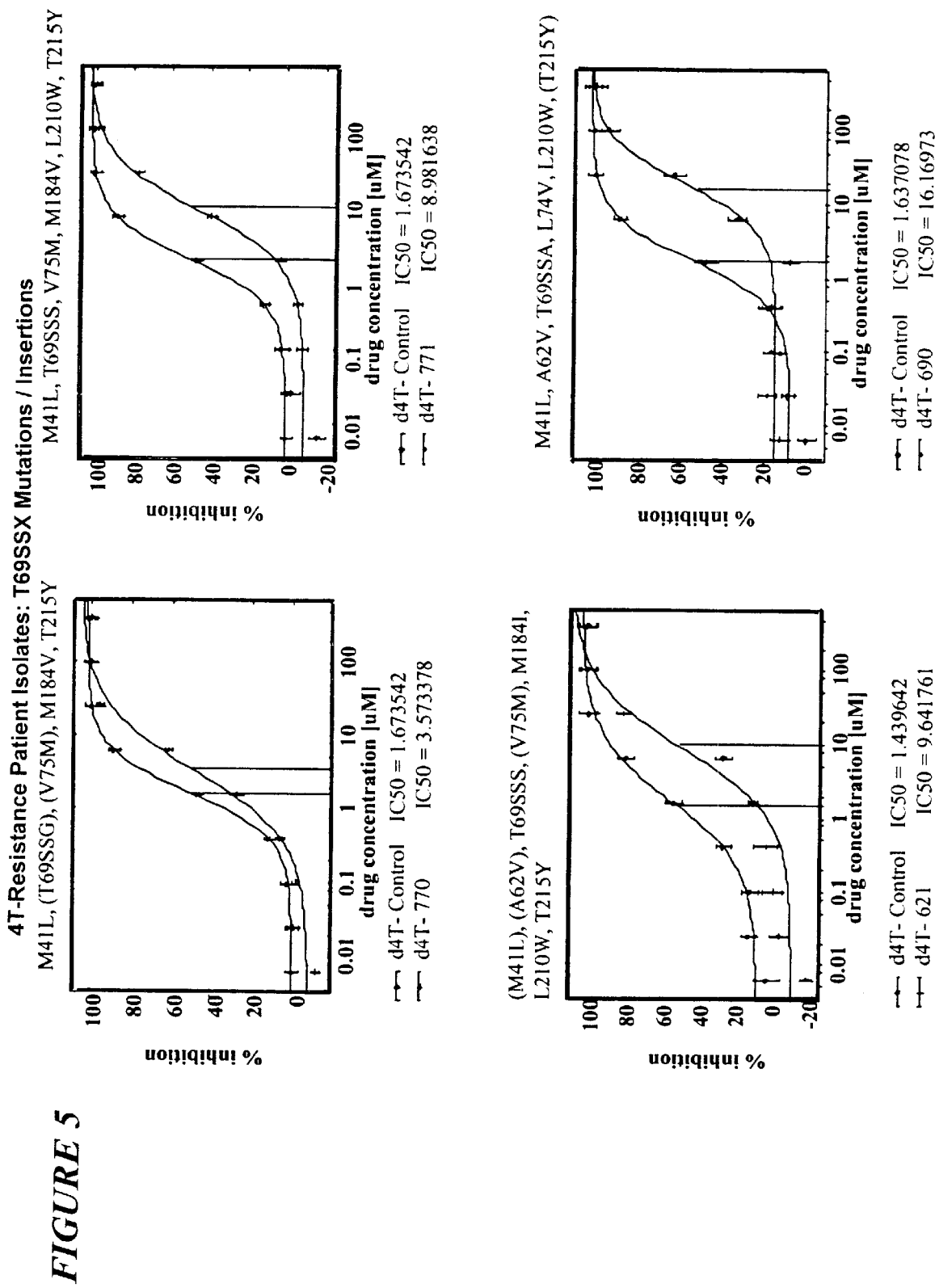
Figure 6:
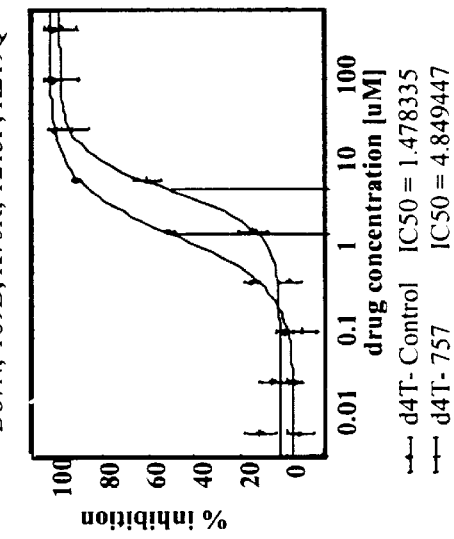
Figure 6:
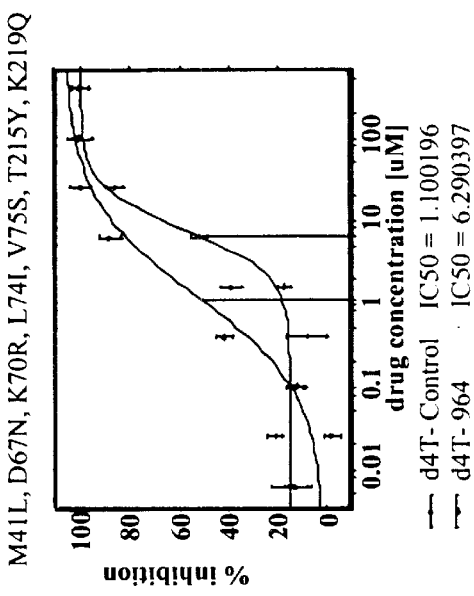
Figure 6:
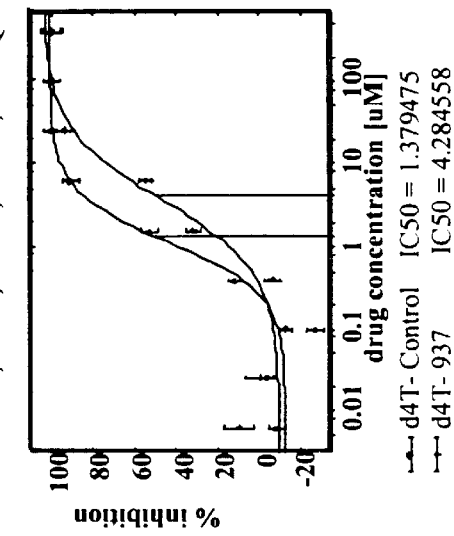
Figure 6:
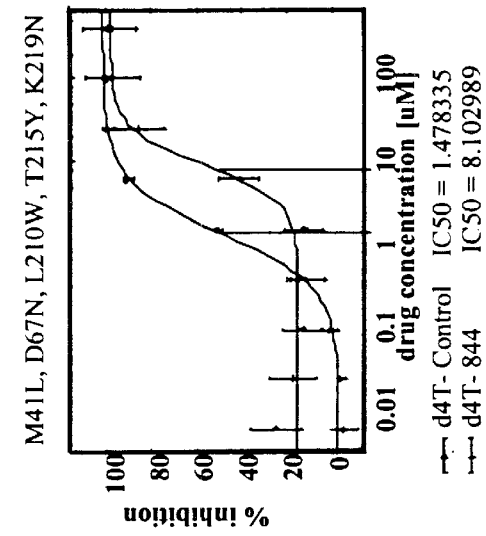
Figure 7:
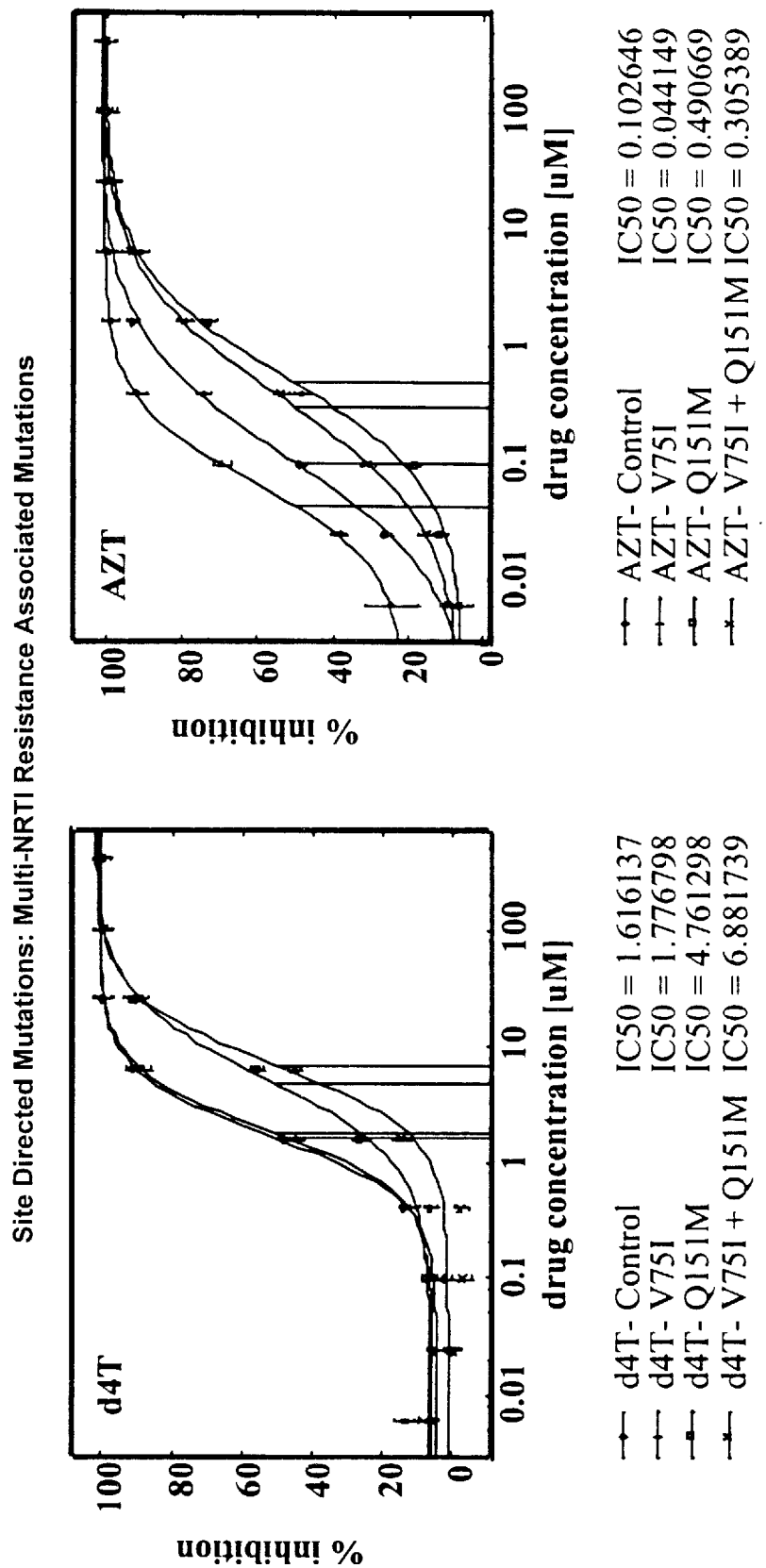
Figure 8:
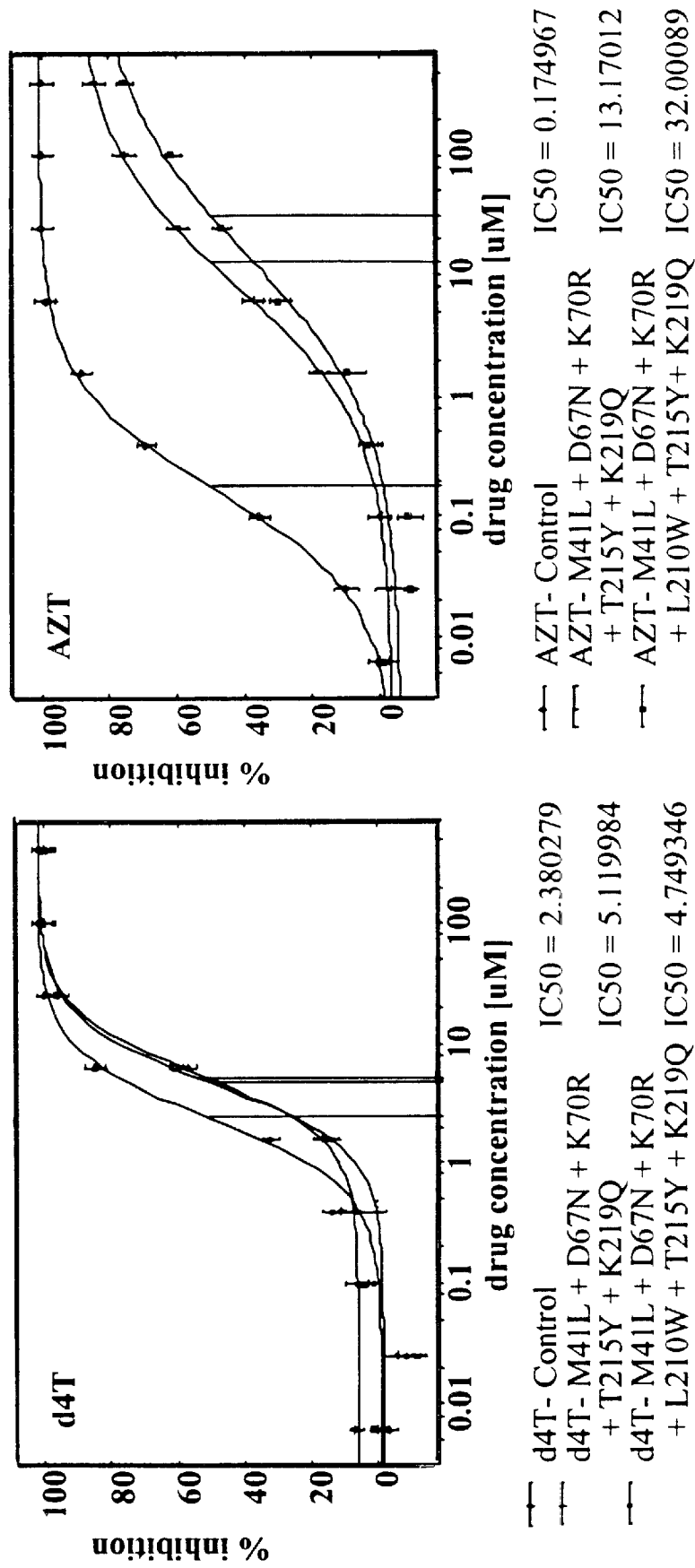
Figure 9:
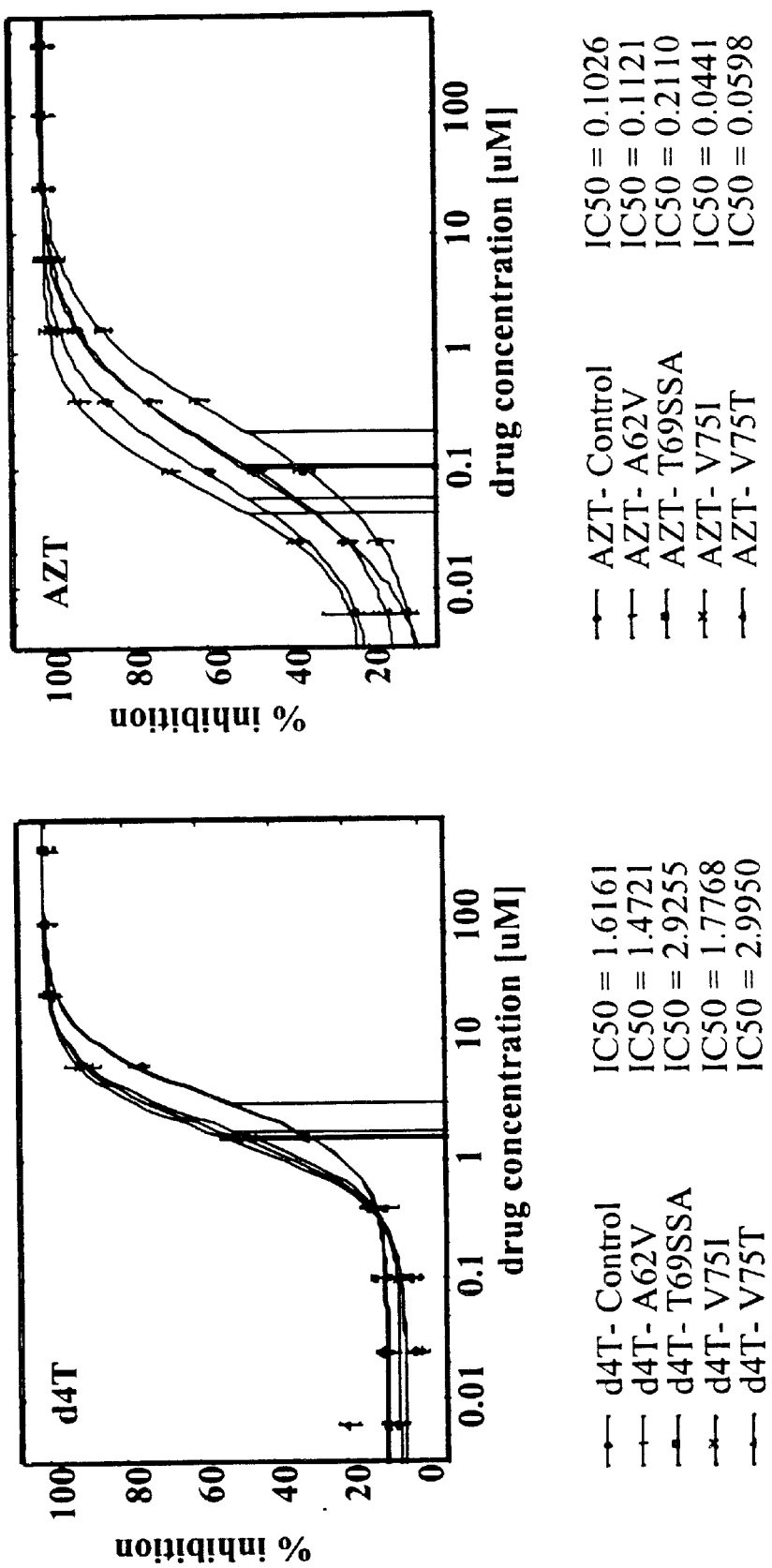
Figure 10:
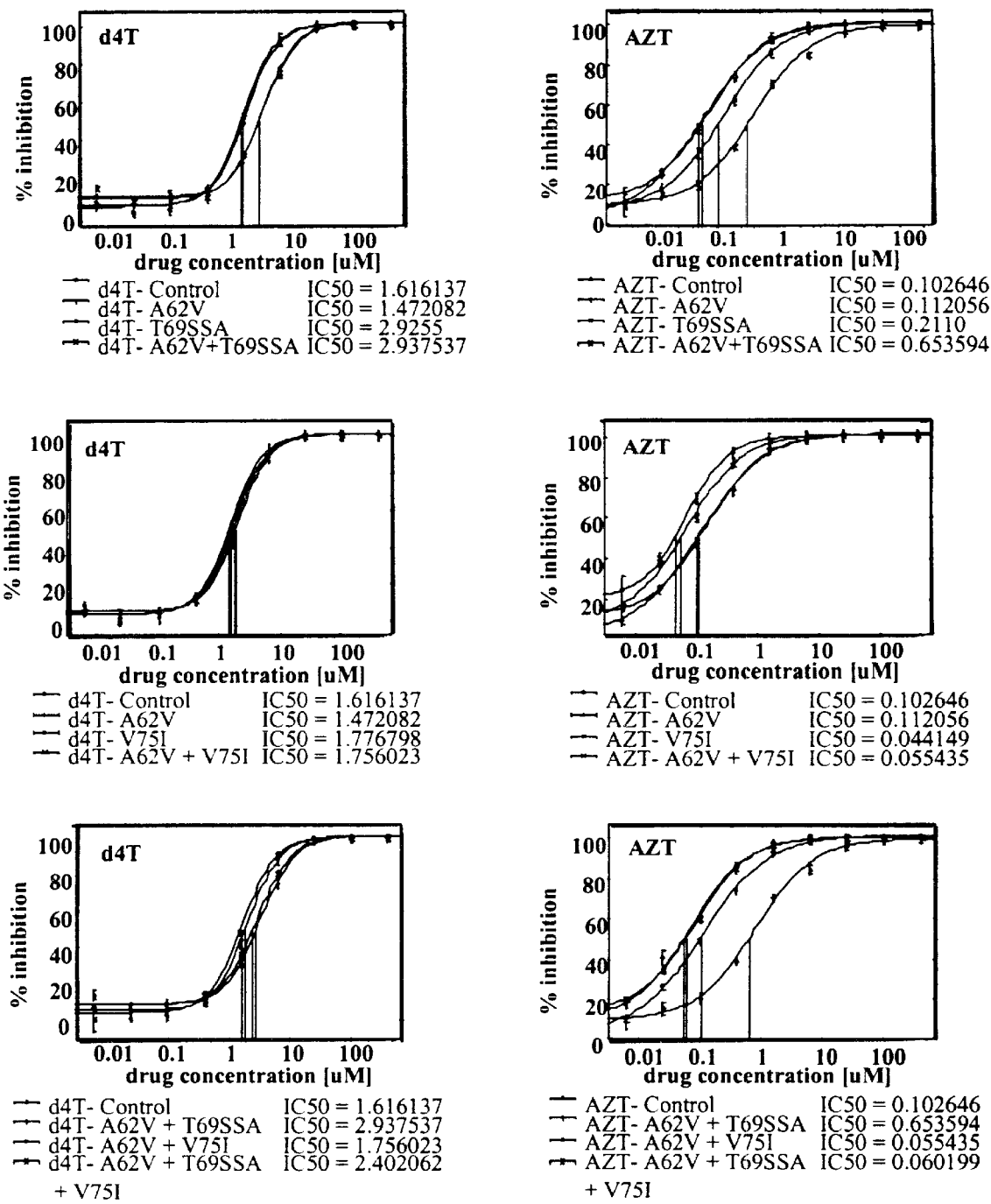
Figure 11:
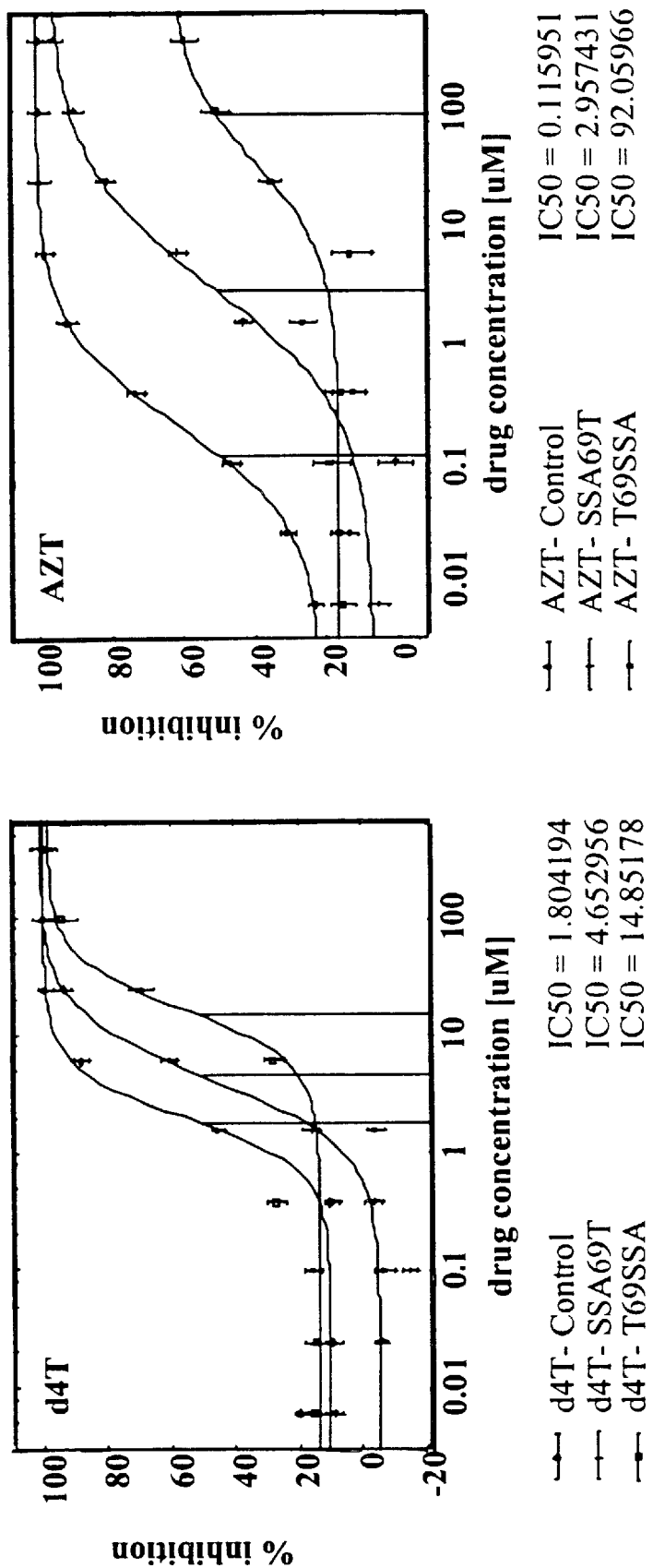
Figure 12:
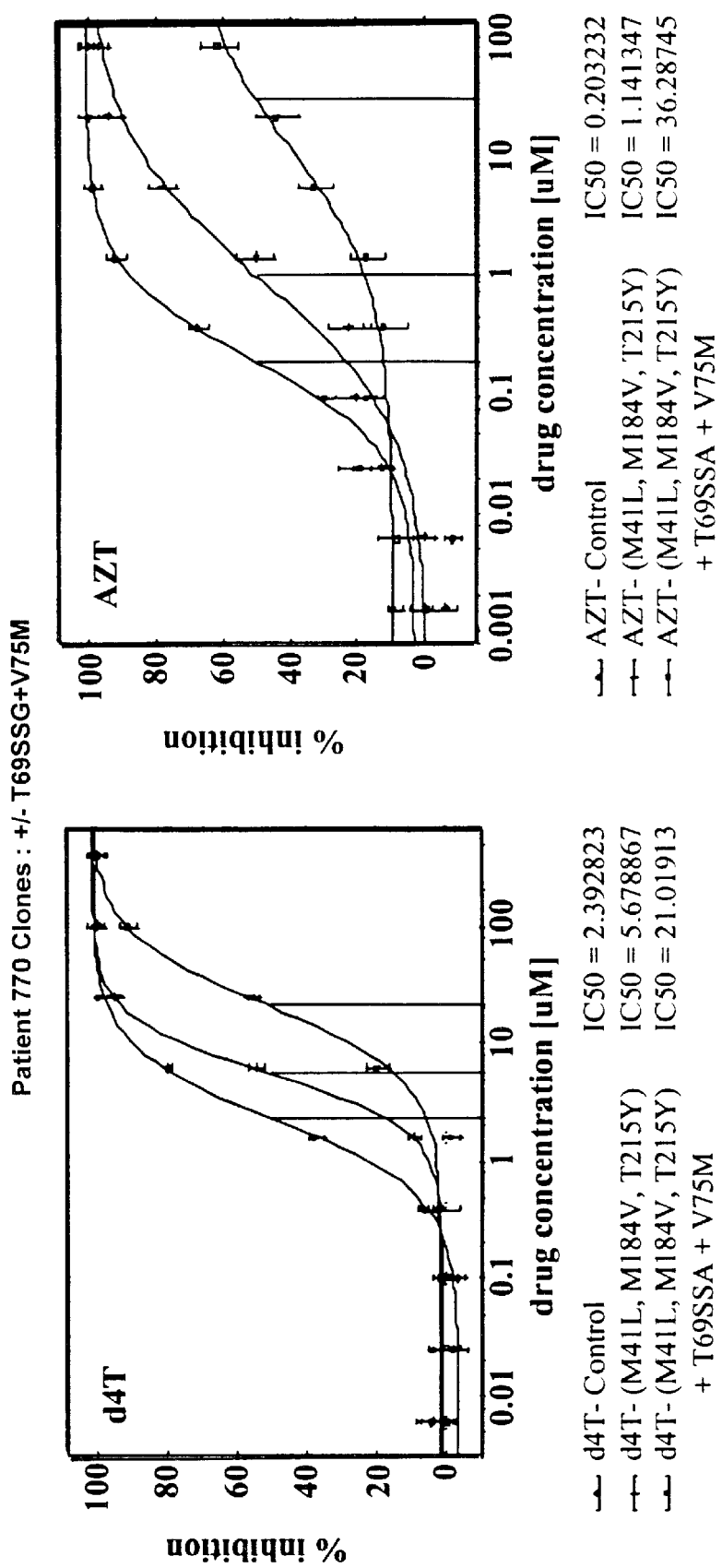
Figure 13:
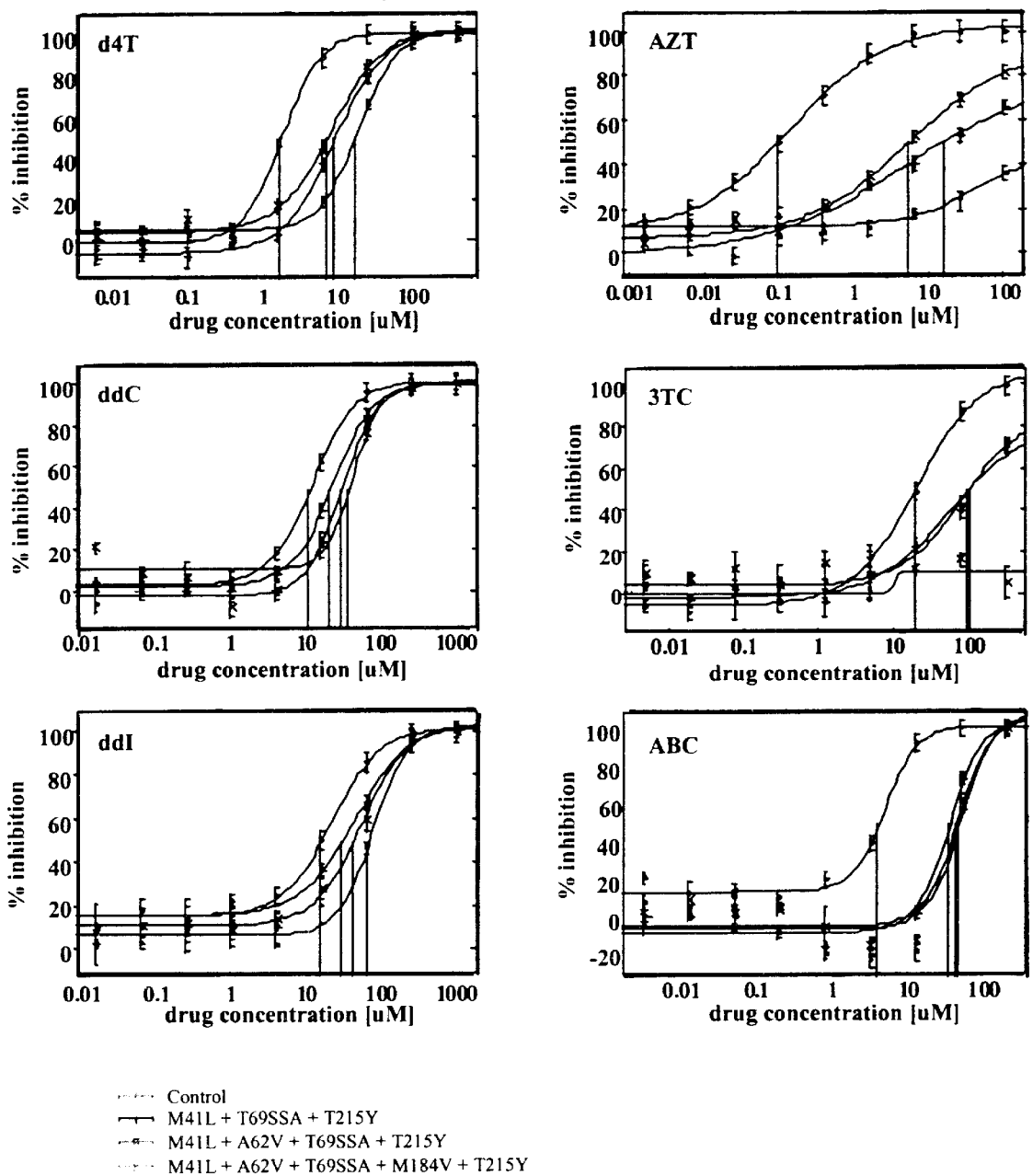

In a preferred embodiment of this invention, evaluation of whether amino acid position 69 of HIV-1 reverse transcriptase was wild type or mutant was carried out using a phenotypic susceptibility assay using resistance test vector DNA prepared from the biological sample. In one embodiment, plasma sample was collected, viral RNA was purified and an RT-PCR methodology was used to amplify a patient derived segment encoding the HIV-1 protease and reverse transcriptase regions. The amplified patient derived segments were then incorporated, via DNA ligation and bacterial transformation, Canto an indicator gene viral vector thereby generating a resistance test vector. Resistance test vector DNA was isolated from the bacterial culture and the phenotypic susceptibility assay was carried out as described in Example 1. The results of the phenotypic susceptibility assay with patient samples having a T69SSX mutation/insertion is shown in FIG. 5. The nucleic acid (DNA) sequence of the patient derived HIV-1 protease and reverse transcriptase regions from patient samples 621, 690, 770, 771 was determined using a fluorescence detection chain termination cycle sequencing methodology (ABI/PE). The method was used to determine a consensus nucleic acid sequence representing the combination of sequences of the mixture of HIV-1 variants existing in the subject sample (representing the quasispecies), and to determine the nucleic acid sequences of individual variants.

Phenotypic susceptibility profiles of patient samples and site directed mutants showed a significant reduction in d4T susceptibility (increased resistance) AZT susceptibility correlated with a mutation in the nucleic acid sequence encoding the amino acids serine, serine, serine (SSS), serine, serine, alanine (SSA) or serine, serine, glycine(SSG) at position 69 of HIV-1 reverse transcriptase and the presence of mutations at some subset of the positions described above. These positions include those previously associated with NRTI-resistance (41, 67, 70, 74, 75, 184, 210, 215, and 219) or the positions observed to be mutated in these patients which have been previously uncharacterized (1, 6, 9, 20, 21, 33, 39, 43, 44, 64, 68, 99, 109, 115, 118, 138, 158, 167, 173, 174, 177, 179, 196, 202, 211, 218, 221, 228, 240, 241, 283, 284, 288, 291, 297).

Phenotypic susceptibility profiles of patient samples with insertions at 69 showed decreased susceptibility to AZT, 3TC, ddC, ddI, d4T, and abacavir.

Phenotypic and Genotypic Correlation of Mutations at Amino Acids 62, 75, 77, 116 and 115 of HIV-1 Reverse Transcriptase Phenotypic susceptibility profiles of patient samples and site directed mutants showed decreases in susceptibility to NRTIs (AZT, ddC, ddI, 3TC, d4T and abacavir) when the positions 62, 75, 77, 116 and 115 or some subset of those positions contained amino acids 62V, 75I, 77L, 116F, or 151M in HIV-1 reverse transcriptase. The presence of additional mutations at positions 41, 67, 69, 184, 210, 215 and 219 could further modify (increase or decrease) susceptibility to the NRTIs.

Phenotypic and Genotypic Correlation of Mutations Previously Associated with AZT-resistance to d4T-resistance in HIV-1 Reverse Transcriptase Phenotypic susceptibility profiles of patient samples and site directed mutants showed significant decreases in susceptibility to d4T when mutations were present at positions previously correlated with loss of susceptibility to AZT (41, 67, 70, 210, 215, and 219) and also at some subset of positions previously correlated with loss of susceptibility to other NRTIs (74, 75, 184) or with previously uncharacterized mutations observed in the patient viruses described above (1, 6, 9, 20, 21, 33, 39, 43, 44, 64, 68, 99, 109, 115, 118, 138, 158, 167, 173, 174, 177, 179, 196, 202, 211, 218, 221, 228, 240, 241, 283, 284, 288, 291, 297).

Table of phenotypes associated with specific mutations introduced into RTV
Average fold reduction in susceptibility observed in HIV based resistance test vectors containing specific mutations (number of replicates tested)

|  | AZT | ddC | ddI | 3TC | d4T | ABC |
|---|---|---|---|---|---|---|
| A62V (3) | 1.25 | 0.74 | 0.84 | 0.54 | 0.84 | 0.59 |
| T69SSA (3) | 1.98 | 1.55 | 1.32 | 3.20 | 1.58 | 2.52 |

-continued

Table of phenotypes associated with specific mutations
introduced into RTV
Average fold reduction in susceptibility observed in HIV based resistance test
vectors containing specific mutations (number of replicates tested)

|   | AZT | ddC | ddI | 3TC | d4T | ABC |
|---|---|---|---|---|---|---|
| 62 + 69 (4) | 6.87 | 1.74 | 1.54 | 2.89 | 1.66 | 2.71 |
| 62 + 69 + 215 (1) | >1000 | 1.34 | 2.52 | 14.82 | 6.97 | 9.84 |
| 62 + 69 + 74V(1) | 1.49 | 1.80 | 1.92 | 2.46 | 1.50 | 3.07 |
| 62 + 69 + 75I(1) | 0.71 | 1.89 | 1.17 | 4.08 | 1.40 | 2.56 |
| 41 + 215 (4) | 17.82 | 1.21 | 1.09 | 1.89 | 1.61 | 1.68 |
| 41 + 210 + 215 (3) | 56.14 | 1.36 | 1.08 | 2.14 | 1.94 | 2.25 |
| 41 + 69 + 215 (2) | 141.71 | 1.41 | 2.02 | 6.27 | 5.20 | 9.69 |
| 41 + 62 + 69 + 215 (3) | >1000 | 1.67 | 2.61 | 8.10 | 7.99 | 9.68 |
| 41 + 69 + 210 + 215 (3) | >1000 | 2.97 | 3.48 | 16.99 | 10.18 | 13.90 |
| 41 + 69 + 75M + 210 + 215 (1) | >1000 | 2.86 | 3.49 | 17.10 | 11.41 | 19.34 |
| 41 + 62 + 69 + 210 + 215 (3) | >1000 | 2.10 | 3.02 | 21.98 | 13.30 | 16.41 |
| 41 + 62 + 69 + 75M + 210 + 215 (1) | >1000 | 2.09 | 3.10 | 18.41 | 13.18 | 15.53 |
| 41 + 62 + 69 + 75S + 210 + 215 (1) | >1000 | 2.58 | 5.12 | 31.67 | 14.13 | 14.21 |
| 41 + 215 (4) | 17.82 | 1.21 | 1.09 | 1.89 | 1.61 | 1.68 |
| 41 + 184 + 215 (3) | 2.77 | 1.73 | 1.35 | >110 | 1.18 | 3.02 |
| 41 + 69 + 215 (2) | 141.71 | 1.41 | 2.02 | 6.27 | 5.20 | 9.69 |
| 41 + 69 + 184 + 215 (2) | 5.87 | 3.48 | 2.28 | >110 | 2.32 | 11.56 |
| 41 + 62 + 69 + 215 (3) | >1000 | 1.67 | 2.61 | 8.10 | 7.99 | 9.68 |
| 41 + 62 + 69 + 184 + 215 (2) | 43.86 | 2.90 | 2.55 | >110 | 3.98 | 11.73 |

What is claimed is:

1. A method of assessing the effectiveness of nucleoside reverse transcriptase antiretroviral therapy of an HIV-infected patient comprising:

(a) collecting a plasma sample from the HIV-infected patient; and (b) evaluating whether the plasma sample contains nucleic acid encoding HIV reverse transcriptase having a mutation at codon 69; wherein the mutation results in a substitution of threonine with serine-serine-X, wherein X is an amino acid selected from the group consisting of alanine, glycine, and serine, in which the presence of the mutation at codon 69 correlates with decreased susceptibility to d4T.

2. The method of claim 1, wherein the mutation at codon 69 results in a substitution of threonine with serine-serine-alanine.

3. The method of claim 1, wherein the mutation at codon 69 results in a substitution of threonine with serine-serine-glycine.

4. The method of claim 1, wherein the mutation at codon 69 results in a substitution of threonine with serine-serine-serine.

5. The method of claim 1, wherein the reverse transcriptase has additional mutations, wherein the additional mutations result in (i) a substitution of methionine at codon 41 with leucine; and (ii) a substitution of threonine at codon 215 with tyrosine.

6. The method of claim 1, wherein the HIV-infected patient is being treated with an antiretroviral agent.

7. The method of claim 5, wherein reverse transcriptase has an additional mutation at codon 210, wherein the mutation at codon 210 results in a substitution of leucine with tryptophan.

8. The method of claim 5, wherein reverse transcriptase has an additional mutation at codon 62, wherein the mutation at codon 62 results in a substitution of alanine with valine.

9. The method of claim 8, wherein reverse transcriptase has an additional mutation at codon 210, wherein the mutation at codon 210 results in a substitution of leucine with tryptophan.

10. The method of claim 7, wherein the reverse transcriptase has an additional mutation at codon 75, wherein the mutation at codon 75 results in a substitution of valine with methionine.

11. The method of claim 1, wherein reverse transcriptase has additional mutations at codon 62 and codon 215, wherein the mutation at codon 62 results in a substitution of alanine with valine, and the mutation at codon 215 results in a substitution of threonine with tyrosine or phenylalanine.

12. The method of claim 1, wherein reverse transcriptase has additional mutations at codon 62 and codon 74, wherein the mutation at codon 62 results in a substitution of alanine with valine, and the mutation at codon 74 results in a substitution of leucine with valine.

13. A method of assessing the effectiveness of antiretroviral therapy of an HIV-infected patient comprising:

(a) collecting a biological sample from an HIV-infected patient; and (b) evaluating whether the biological sample comprises nucleic acids encoding HIV reverse transcriptase having a mutation at codons 41, 67, 210, 215 and 219, wherein the mutation at codon 41 results in a substitution of methionine with leucine, wherein the mutation at codon 67 results in a substitution of aspartic acid with aspargine, wherein the mutation at codon 210 results in a substitution of leucine with tryptophan, wherein the mutation at codon 215 results in a substitution of threonine with tyrosine, wherein the mutation at codon 219 results in a substitution of lysine with glutamine, and wherein the presence of the mutations correlate with a decrease in d4T susceptibility.

* * * * *